US011988802B2

(12) United States Patent
Craddock et al.

(10) Patent No.: US 11,988,802 B2
(45) Date of Patent: May 21, 2024

(54) ESTIMATING MINERALOGY AND RECONSTRUCTING ELEMENTS OF RESERVOIR ROCK FROM SPECTROSCOPY DATA

(71) Applicant: Schlumberger Technology Corporation, Sugar Land, TX (US)

(72) Inventors: Paul Ryan Craddock, Scituate, MA (US); Lalitha Venkataramanan, Lexington, MA (US); Prakhar Srivastava, Pune (IN); Harish Baban Datir, Tananger (NO)

(73) Assignee: Schlumberger Technology Corporation, Sugar Land, TX (US)

( * ) Notice: Subject to any disclaimer, the term of this patent is extended or adjusted under 35 U.S.C. 154(b) by 404 days.

(21) Appl. No.: 17/438,340

(22) PCT Filed: Mar. 9, 2020

(86) PCT No.: PCT/US2020/021774
§ 371 (c)(1),
(2) Date: Sep. 10, 2021

(87) PCT Pub. No.: WO2020/185716
PCT Pub. Date: Sep. 17, 2020

(65) Prior Publication Data
US 2022/0179121 A1 Jun. 9, 2022

Related U.S. Application Data

(60) Provisional application No. 62/816,347, filed on Mar. 11, 2019.

(51) Int. Cl.
*G01V 5/10* (2006.01)
*E21B 49/00* (2006.01)
(Continued)

(52) U.S. Cl.
CPC .............. *G01V 5/101* (2013.01); *E21B 49/00* (2013.01); *E21B 49/005* (2013.01); *G01N 33/24* (2013.01);
(Continued)

(58) Field of Classification Search
CPC ........ E21B 49/00; E21B 49/005; E21B 49/02; E21B 2200/20; E21B 2200/22;
(Continued)

(56) References Cited

U.S. PATENT DOCUMENTS 6,376,838 B1    4/2002  Odom
6,884,994 B2    4/2005  Simonetti et al.
(Continued)

FOREIGN PATENT DOCUMENTS

WO          WO-0122123 A1 *  3/2001  ............. G01V 11/00

OTHER PUBLICATIONS

Freedman, R et al., "New Method for Determining Mineralogy and Matrix Properties from Elemental Chemistry Measured by Gamma Ray Spectroscopy Logging Tools", SPE 170722, presented at the SPE Annual Technical Conference and Exhibition, Amsterdam, The Netherlands, 2014, 16 pages.
(Continued)

*Primary Examiner* — Mark R Gaworecki
(74) *Attorney, Agent, or Firm* — Jeffrey D. Frantz

(57) ABSTRACT

Methods and systems are provided to learn and apply a mapping function from data representing concentrations of atomic elements in a geological formation (or other data corresponding thereto) to mineral component concentrations in the geological formation (and/or from mineral component concentrations to reconstructed elemental concentrations in the geological formation). The mapping function can be derived from a trained neural network (such as an autoencoder). The output of the mapping function can be used to (Continued)

determine estimates of one or more formation properties, such as formation matrix density, formation porosity, matrix Sigma, formation saturation, other formation property, or combinations thereof.

20 Claims, 11 Drawing Sheets

(51) Int. Cl.
| | |
|---|---|
| *G01N 33/24* | (2006.01) |
| *G06N 3/04* | (2023.01) |
| *G06N 3/045* | (2023.01) |
| *G06N 3/08* | (2023.01) |
| *G06N 3/084* | (2023.01) |
| *G06N 3/088* | (2023.01) |
| *E21B 49/02* | (2006.01) |
| *G06N 3/082* | (2023.01) |

(52) U.S. Cl.
CPC .............. *G06N 3/045* (2023.01); *G06N 3/08* (2013.01); *G06N 3/084* (2013.01); *G06N 3/088* (2013.01); *E21B 49/02* (2013.01); *E21B 2200/20* (2020.05); *E21B 2200/22* (2020.05); *G06N 3/082* (2013.01)

(58) Field of Classification Search
CPC ........ G01N 33/24; G01V 5/101; G06N 3/045; G06N 3/08; G06N 3/082; G06N 3/084; G06N 3/088

See application file for complete search history.

(56) References Cited

U.S. PATENT DOCUMENTS

| | | | |
|---|---|---|---|
| 7,309,983 | B2 | 12/2007 | Freedman |
| 7,366,615 | B2 | 4/2008 | Herron et al. |
| 9,874,551 | B2 | 1/2018 | Herron et al. |
| 2014/0116776 | A1 | 5/2014 | Marx et al. |
| 2014/0214324 | A1 | 7/2014 | Freedman et al. |
| 2016/0266275 | A1 | 9/2016 | Akkurt et al. |
| 2017/0115428 | A1* | 4/2017 | Zhou .................. G01V 5/045 |
| 2017/0241921 | A1 | 4/2017 | Chen |
| 2017/0200290 | A1 | 7/2017 | Bhattiprolu |

OTHER PUBLICATIONS

Gal, Y. et al., "Dropout as a Bayesian Approximation: Representing Model Uncertainty in Deep Learning", presented at the Proceedings of the 33rd International Conference on Machine Learning, New York, New York, USA, 2016, 10 pages.
Gal, Y. et al., "Concrete Dropout", presented at the 31st Conference on Neural Information Processing Systems, Long Beach, California, USA, 2017, 10 pages.
He, K. et al., "Delving Deep into Rectifiers: Surpassing Human-Level Performance on ImageNet Classification", IEEE International Conference on Computer Vision (ICCV), 2015, pp. 1026-1034.
Herron, M. M. et al., "A Robust Permeability Estimator for Siliciclastics", SPE 49301, presented at the SPE Annual Technical Conference and Exhibition, New Orleans, Louisiana, USA, 1998, pp. 777-787.
Herron, S. L. et al., "Quantitative Lithology: An Application for Open and Cased Hole Spectroscopy", presented at the SPWLA 37th Annual Logging Symposium, New Orleans, Louisiana, USA, 1996, 25 pages.
Hertzog, R. C., "Laboratory and Field Evaluation of an Inelastic Neutron Scattering and Capture Gamma Ray Spectrometry Tool", Society of Petroleum Engineers Journal, 1980, pp. 327-340.
Krizhevsky, A. et al., "ImageNet Classification with Deep Convolutional Neural Networks", presented at the 31st Conference on Neural Information Processing Systems, Lake Tahoe, Nevada, USA, 2012, 9 pages.
Lakshminarayanan, B. et al., "Simple and Scalable Predictive Uncertainty Estimation using Deep Ensembles", presented at the 31st Conference on Neural Information Processing Systems, Long Beach, California, USA, 2017, 12 pages.
Mayer, C. et al., "Global, A New Approach to Computer-Processed Log Interpretation", SPE 9341, presented at the 55th Annual Fall Technical Conference and Exhibition of the Society of Petroleum Engineers of AIME, Dallas, Texas, USA, 1980, 14 pages.
Radtke, R. J. et al., "A New Capture and Inelastic Spectroscopy Tool Takes Geochemical Logging to the Next Level", presented at the 53rd Annual Logging Symposium, Cartagena, Colombia, 2012, 16 pages.
International Search Report and Written Opinion of related International Patent Application No. PCT/US2020/021774 dated Jul. 3, 2020, 11 pages.
International Preliminary Report on Patentability of related International Patent Application No. PCT/US2020/021774 dated Sep. 23, 2021, 10 pages.
Valentin, M. B., "Deep Learning Methods of Geological Reservoir Borehole Log Images and Applications", 2018, downloaded from the Internet at [www.researchgate.net/publication/336587891_Deep_learning_medhods_on_geological_reservoir_borehole_log_images_and_applications], 221 pages.
Mahmoodi, O. et al., "Supervised classification of down-hole physical properties measurements using neural network to predict the lithology", Journal of Applied Geophysics, 2016, 124, pp. 17-26.
Li, H. et al., "Prediction of Subsurface NMR T2 Distributions in a Shale Petroleum System Using Variational Autoencoder-Based Neural Networks", IEEE Geoscience and Remote Sensing Letters, 2017, 14(12), 3 pages.
Extended European search report issued in European Patent Application No. 20769015.7 dated Oct. 18, 2022, 12 pages.

* cited by examiner

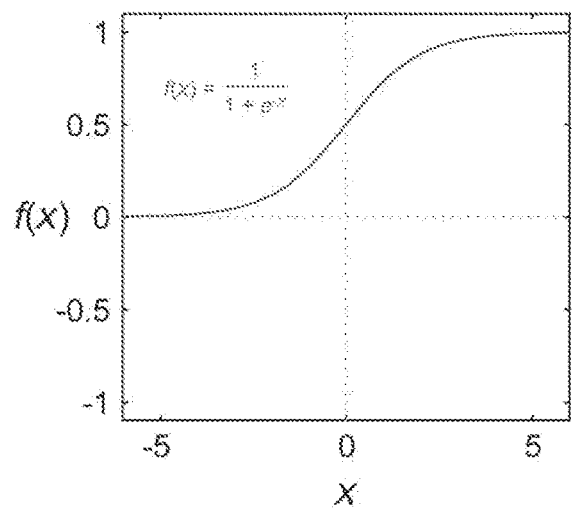
FIG. 6A sigmoid activation
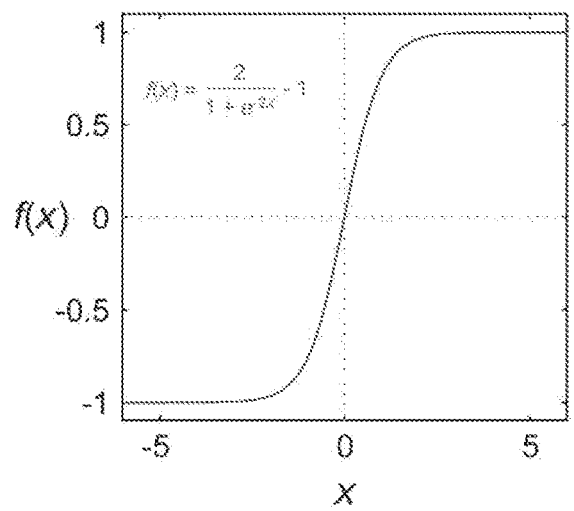
FIG. 6B tanh activation
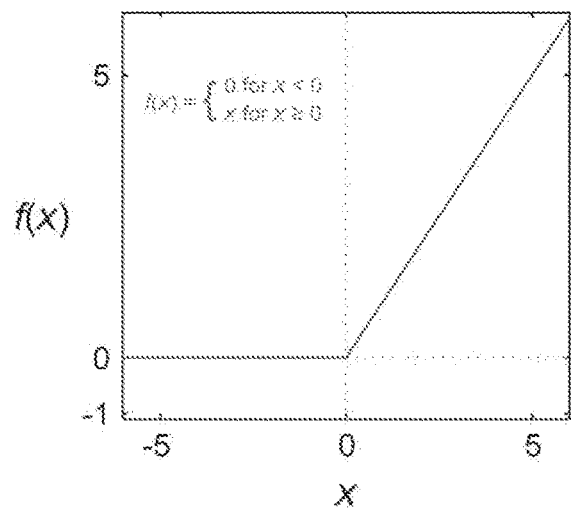
FIG. 6C ReLU activation
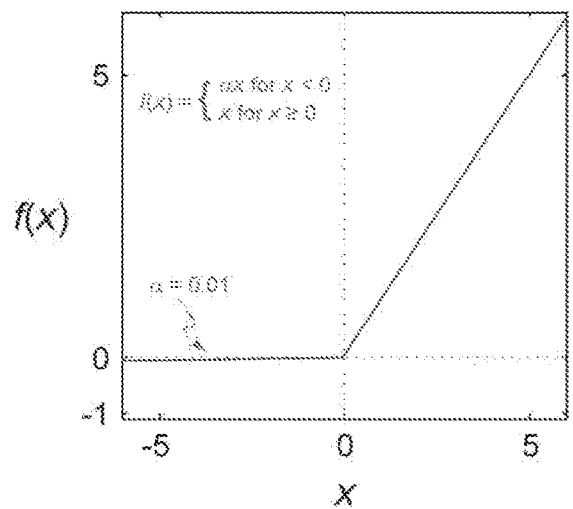
FIG. 6D Leaky ReLU activation

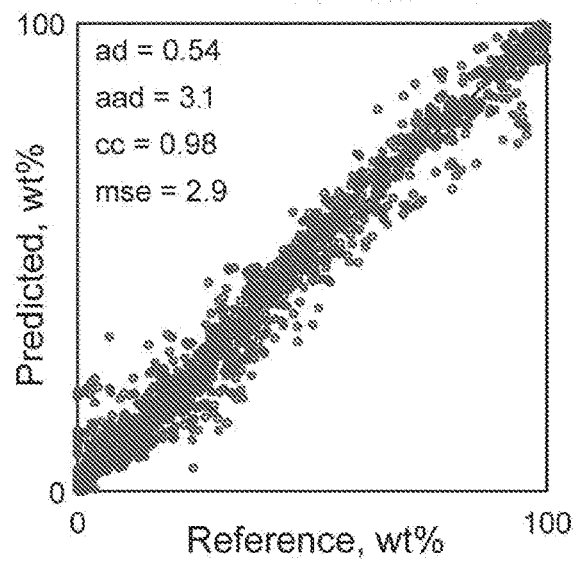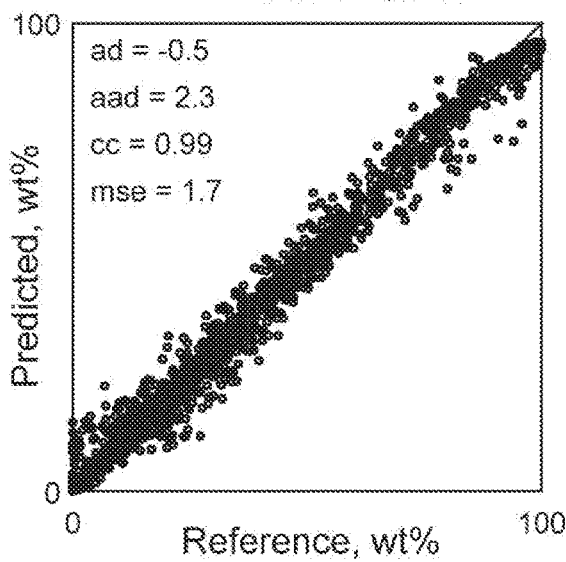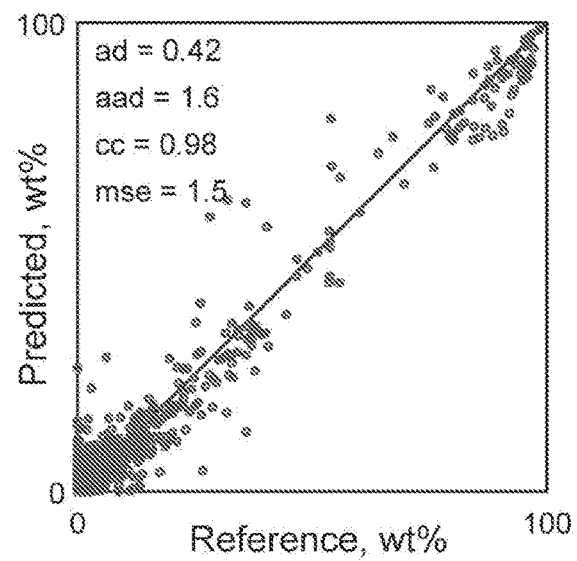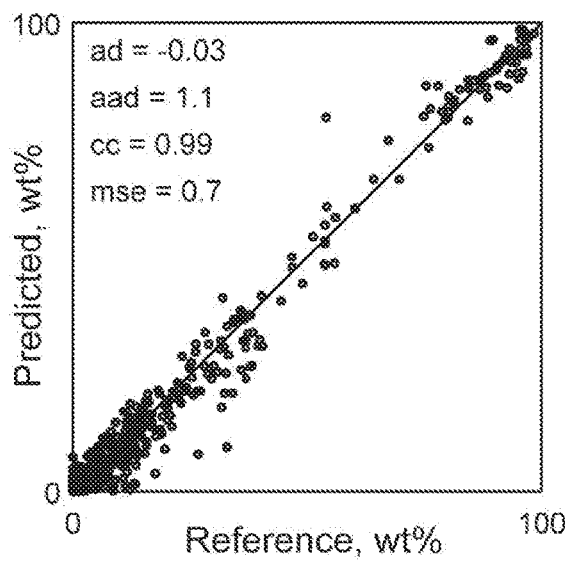

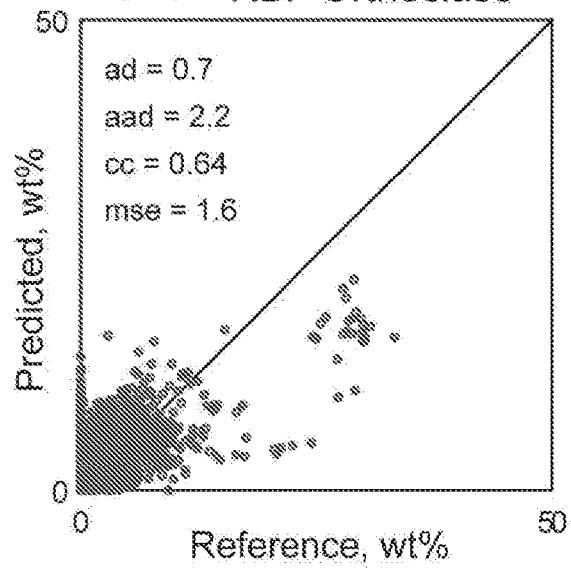
FIG. 9E RBF Orthoclase
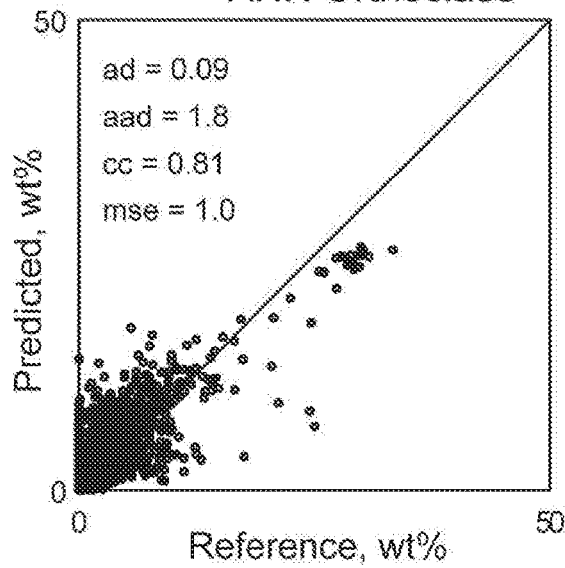
FIG. 9F ANN Orthoclase
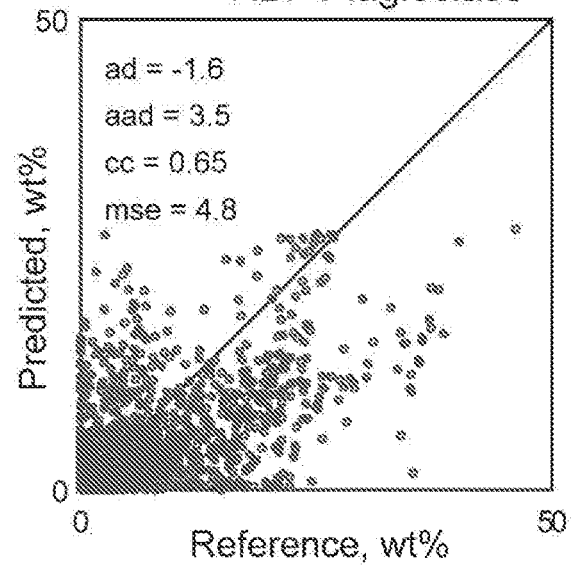
FIG. 9G RBF Plagioclase
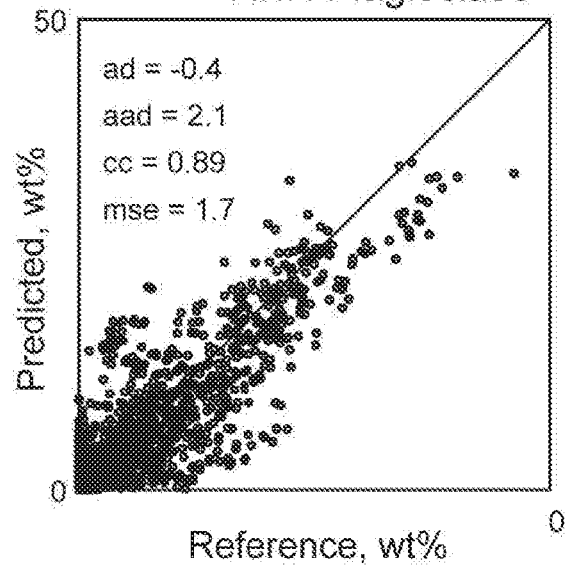
FIG. 9H ANN Plagioclase

ESTIMATING MINERALOGY AND RECONSTRUCTING ELEMENTS OF RESERVOIR ROCK FROM SPECTROSCOPY DATA

CROSS-REFERENCE TO RELATED APPLICATIONS

This application is a National Stage Entry of International Application No. PCT/US2020/021774, filed Mar. 9, 2020, which claims the benefit of U.S. Provisional Application No. 62/816,347, filed Mar. 11, 2019.

BACKGROUND

1. Field

The present disclosure relates to methods and apparatus to characterize geological rock formations.

2. State of the Art

When evaluating a geological rock formation for oil, natural gas or other materials, it is beneficial to determine or estimate characteristics or properties of formation. For example, formation properties such as porosity, permeability, and water saturation can be useful for estimating the hydrocarbon content of the formation. Such formation properties can also be useful in making drilling decisions based on estimated mechanical properties of the formation as well as developing completion strategies for producing hydrocarbons from the formation.

Accurate quantification of mineral phases or components in the reservoir rock is an essential part of the petrophysical evaluation of geological rock formations. Mineral component concentrations (hereafter referred to simply as mineralogy) dictate bulk rock properties such as matrix (grain) density, acoustic slowness, electrical conductivity (or its inverse electrical resistivity), dielectric permittivity, macroscopic nuclear cross sections, among other properties. Rock properties influence the bulk formation response of numerous logging sonde measurements. Rock properties must be known to correctly interpret borehole log measurements to produce an estimate of relevant petrophysical properties of the rock formation, such as porosity, permeability, water saturation, and hydrocarbon saturation. The same mineralogy information may be further used to correlate, stratigraphically or otherwise, measurements across multiple boreholes.

Methods and apparatus to determine mineralogy in a geological rock formation from rock samples brought to the surface, for example performed in a surface laboratory or surface well site, are well known to those skilled in the art. These methods include X-ray diffraction and infrared spectroscopy. These methods may be considered 'direct measurements' of mineralogy because each produces a spectrum in which is comprised information about the mineral identity (position of the spectrum signal, generally plotted on the horizontal axis) and about the mineral component concentration (intensity of the spectrum signal, generally plotted on the vertical axis). These methods are not available downhole within a borehole.

The determination of mineralogy in a geological rock formation from borehole logging measurements is more challenging because the determination relies upon 'indirect measurements'. A logging measurement commonly used to infer mineralogy is induced-neutron gamma ray spectroscopy/spectrometry. The principles of this logging technique are well known to those skilled in the art, and are described in detail elsewhere (e.g., Hertzog, R. C., 1980, "Laboratory and field evaluation of an inelastic neutron scattering and capture gamma ray spectrometry tool," Society of Petroleum Engineers Journal, 20, 327-340; Herron, S. L. and Herron, M. M., 1996, "Quantitative lithology: An application for open and cased hole spectroscopy," SPWLA 37th Annual Logging Symposium, New Orleans, Louisiana, USA, June 16-19; and Radtke, R. J., Lorente, M., Adolph, B., Berhide, M., Fricke, S., Grau, J., Herron. S. L., Horkowitz, J., Jorion, B., Madio, D., May, D., Miles, J., Perkins, L., Philip, O., Roscoe, B., Rose, D. and Stoller, C., 2012, "A new capture and inelastic spectroscopy tool takes geochemical logging to the next level," *SPWLA 53$^{rd}$ Annual Logging Symposium*, Cartagena, Colombia, June 16-20. Briefly, fast neutrons and thermal neutrons generated from a naturally radioactive material or pulsed-neutron generator contained within the housing of the logging sonde interact with elemental nuclei in a formation and produce, respectively, prompt (inelastic) and capture gamma radiation in a local volume surrounding the logging sonde. These produced gamma rays traverse the formation with a fraction detected by a gamma ray detector contained within the housing of the logging sonde. From the detector signal is produced a spectrum containing contributions from gamma rays representing the elemental nuclei in the formation. This spectrum is typically plotted as count rate (vertical axis) versus energy (horizontal axis), and comprises information about element identity (from the characteristic energies of the gamma rays) and about element abundance (from the number of counts) for certain atomic elements commonly found in reservoir rocks (e.g., Si, Al, Ca, Mg, K, Fe, S, etc.). This measurement of elemental abundances does not provide a direct measurement of mineralogy because the same limited number of common rock-forming atomic elements are contained within a much larger number of common rock-forming minerals. An example is the element silicon (Si), which is present within the common sedimentary-bearing minerals quartz ($SiO_2$), opal ($SiO_2 \cdot nH_2O$), potassium feldspar ($KAlSi_3O_8$), plagioclase feldspar ($[Na,Ca]Al[Al,Si]Si_2O_8$), and numerous other silicate minerals including clay and mica group minerals. Nonetheless, there is necessarily a relationship between the bulk elemental concentrations of a rock sample and its mineral component concentrations because minerals have by their defined crystallographic structures a limited range of chemical compositions. Consequently, bulk elemental concentrations of a rock sample are dictated by its mineralogy.

Methods exist to derive an estimate of mineralogy from a measurement of bulk elemental concentrations. These methods rely upon the derivation of a one or more mapping functions to forward model the prediction of mineral component concentrations from elemental concentrations. One groups of methods are linear regression models based on empirical linear relationships between the concentrations of one or more atomic elements and a one or more minerals of interest. For example, see U.S. Pat. No. 9,874,551 to Herron et al. "Determining mineralogy of an earth formation using linear regressions." Another group of methods are radial basis functions, alternatively referred to as nearest-neighbor mapping functions as described in Freedman, R., Herron, S. L., Anand, V., Herron, M., May, D. and Rose, D., 2014, "New method for determining mineralogy and matrix properties from elemental chemistry measured by gamma ray spectroscopy logging tools,", *SPE Annual Technical Conference and Exhibition*, Amsterdam, The Netherlands, 27-29

October. A more general description of radial basis functions applied to other formation measurements is provided in U.S. Pat. No. 7,309,983 to Freedman entitled "Method for determining characteristics of earth formations." Such methods have been applied to the determination of formation mineralogy from elemental concentrations derived from gamma ray spectroscopy logging measurements performed in a borehole.

SUMMARY

The present disclosure provides methods and systems that employ a mapping function derived from a trained artificial neural network, wherein the mapping function is configured to determine (i) bulk mineral component concentrations (also referred to as mineralogy or lithology) of a geological formation from the measurement of bulk concentrations of atomic elements in the formation or other data corresponding thereto, and/or (ii) reconstruction of bulk concentrations of atomic elements in the formation from the mineral component concentrations of (i). One or more parameters that characterize the geological formation can be determined from the mineral component concentrations of i) and/or the reconstructed elemental concentrations of ii). For example, such formation parameter(s) can be matrix density, formation porosity, matrix Sigma, formation saturation, other parameter(s), or combinations thereof.

The methods and systems can be applied to the characterization of a part or sample of a geological formation, in which case the derived mineral component concentrations and reconstructed elemental concentrations are vectors (vector of m number of minerals and vector of e number of atomic elements), or can be applied to a plurality of samples or parts of a formation, in which case the derived mineral component concentrations and reconstructed elemental concentrations are matrices (matrix of m number of mineral components by n number of formation parts/samples and matrix of e number of atomic elements by n number of formation parts/samples). A plurality of formation parts or samples can be investigated as a function of depth in a borehole drilled into the Earth's surface, in which case it can be constructed as a depth-log of mineral component concentrations and reconstructed elemental concentrations along the borehole that traverses the formation.

The measured elemental concentrations or corresponding data may be obtained from measurements performed by a downhole logging tool, such as one attached to a wire, a drilling assembly or other conveyance system. In these cases, the downhole tool is placed in a borehole and the measurements are performed on part(s) of the formation that surround the formation. Alternatively, the formation samples can be outcrop, drill core, drill cuttings, and the like. In these cases, measurements of the formation samples are generally performed at the surface.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein:

FIGS. 6A-6D are plots of different activation functions that can be used as part of the autoencoder of FIG. 5.

FIGS. 9A-9H are plots of predicted concentrations of selected minerals (quartz, dolomite, orthoclase, plagioclase) in a set of rock formation samples using an RBF model (from Freedman et al., 2014) and the autoencoder of FIG. 5; FIG. 9A is a plot of predicted concentrations of quartz in the set of rock formation samples using the RBF model; FIG. 9B is a plot of predicted concentrations of quartz in the set of rock formation samples using the autoencoder of FIG. 5; FIG. 9C is a plot of predicted concentrations of dolomite in the set of rock formation samples using the RBF model; FIG. 9D is a plot of predicted concentrations of dolomite in the set of rock formation samples using the autoencoder of FIG. 5; FIG. 9E is a plot of predicted concentrations of orthoclase in the set of rock formation samples using the RBF model; FIG. 9F is a plot of predicted concentrations of orthoclase in the set of rock formation samples using the autoencoder of FIG. 5; FIG. 9G is a plot of predicted concentrations of plagioclase in the set of rock formation samples using the RBF model; and FIG. 9H is a plot of predicted concentrations of plagioclase in the set of rock formation samples using the autoencoder of FIG. 5.

DETAILED DESCRIPTION OF THE PREFERRED EMBODIMENTS

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

Figure 1:
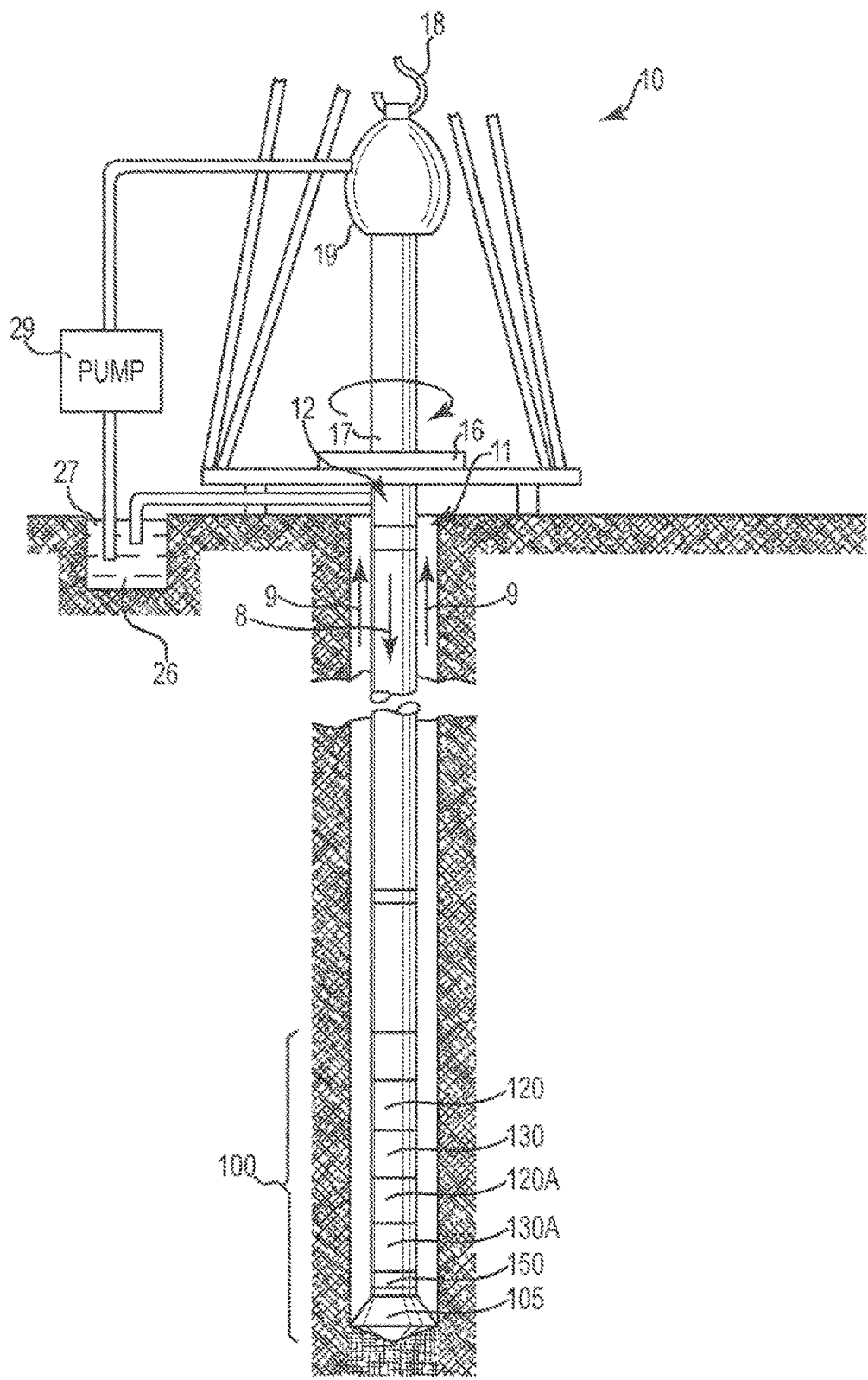
FIG. 1 is a schematic diagram of a wellsite system in accordance with an embodiment of the present disclosure.

FIG. 1 illustrates an embodiment of a wellsite system in accordance with an embodiment of the present disclosure. The wellsite system of FIG. 1 can be onshore or offshore for, for example, exploring and producing oil, natural gas, and other resources that can be used, refined, and otherwise processed for fuel, raw materials and other purposes. In the wellsite system of FIG. 1, a borehole 11 can be formed in subsurface geological rock formation by rotary drilling using any suitable technique. A drillstring 12 can be suspended within the borehole 11 and can have a bottomhole assembly 100 that includes a drill bit 105 at its lower end. A surface system of the wellsite system of FIG. 1 can include a platform and derrick assembly 10 positioned over the borehole 11. The platform and derrick assembly 10 can include a rotary table 16, kelly 17, hook 18 and rotary swivel 19. The drillstring 12 can be rotated by the rotary table 16, energized by any suitable means, which engages the kelly 17 at the upper end of the drillstring 12. The drillstring 12 can be suspended from the hook 18, attached to a traveling block (not shown), through the kelly 17 and the rotary swivel 19, which permits rotation of the drillstring 12 relative to the hook 18. A top drive system could alternatively be used, which can be a top drive system well known to those of ordinary skill in the art.

In the wellsite system of FIG. 1, the surface system can also include drilling fluid or mud 26 stored in a pit 27 formed at the well site. A pump 29 can deliver the drilling fluid 26 to the interior of the drillstring 12 via a port in the swivel 19, causing the drilling fluid to flow downwardly through the drillstring 12 as indicated by the directional arrow 8. The drilling fluid 26 can exit the drillstring 12 via ports in the drill bit 105, and circulate upwardly through the annulus region between the outside of the drillstring 12 and the wall of the borehole 11, as indicated by the directional arrows 9. In this manner, the drilling fluid 26 lubricates the drill bit 105 and carries formation cuttings up to the surface, as the fluid 26 is returned to the pit 27 for recirculation.

In one example, the bottomhole assembly 100 of the wellsite system of FIG. 1 can include one or more of a logging-while-drilling (LWD) module 120, another type of a measuring-while-drilling (MWD) module 130, a rotosteerable system and motor 150, and the drill bit 105. The LWD module 120 can be housed in a special type of drill collar. It will also be understood that more than one LWD module or logging tool within the LWD module can be employed, as generally represented at numeral 120A. As such, references to the LWD module 120 can alternatively mean a module at the position of 120A as well. The LWD module 120 can include capabilities for measuring, processing, and storing information, as well as for communicating with surface equipment.

Figure 2:
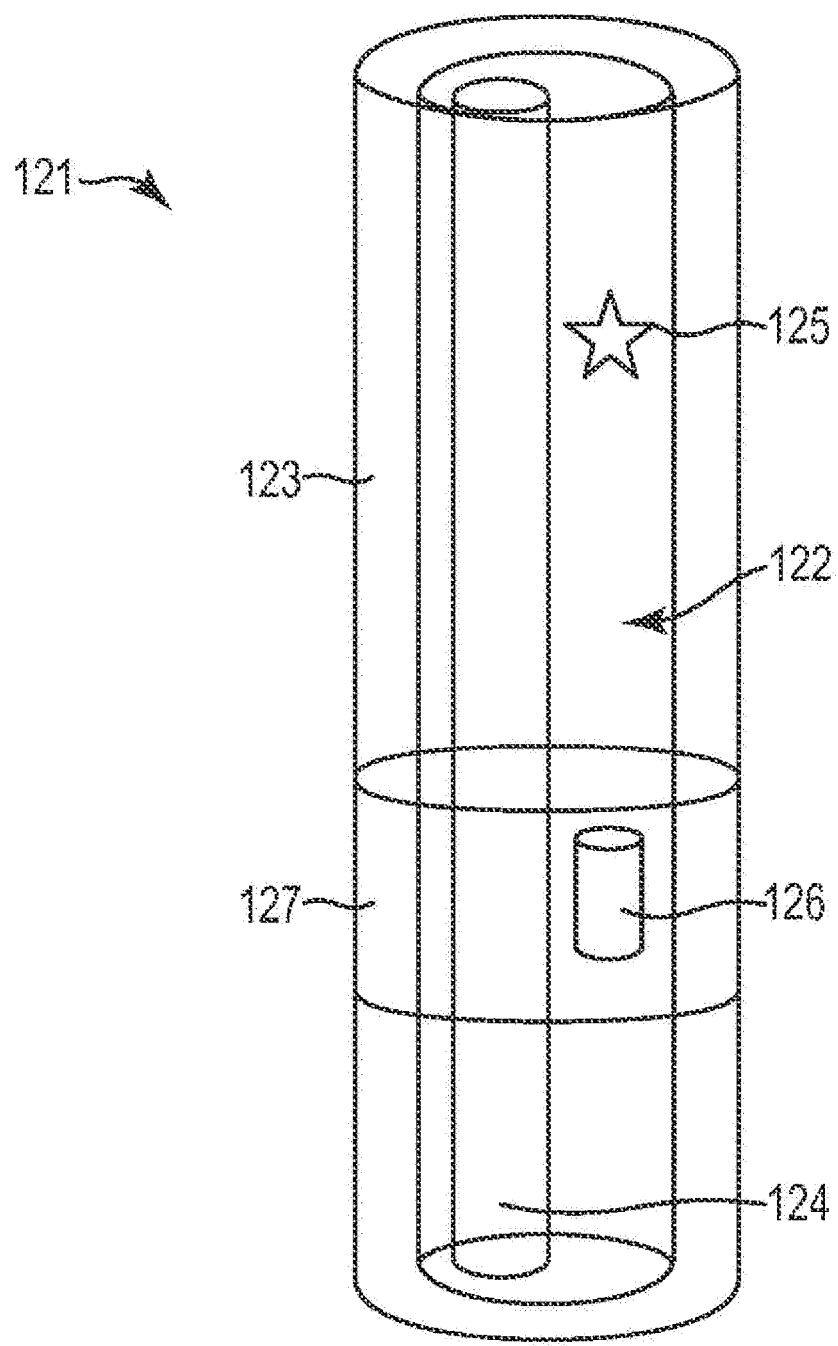
FIG. 2 is a schematic diagram of an exemplary spectroscopy logging tool in accordance with an embodiment of the present disclosure, which can be part of the wellsite system of FIG. 1.

FIG. 2 is a schematic illustration of an exemplary spectroscopic logging tool 121, which can be part of the bottomhole assembly 100 of FIG. 1. The logging tool 121 includes a chassis 122, a collar 123 and a flow tube 124 that extends through the logging tool 121. A neutron source 125 is located at a first location within the logging tool 121 and a detector 126, such as a gamma ray detector, is located at a second location axially spaced from the neutron source 125. A neutron shield such as a boron shield 127 is radially disposed about the logging tool 121 at or near the second location. Specifics regarding this embodiment and other embodiments of spectroscopic tools employing the general configuration or aspects of the logging tool 121 and/or LWD module 120 are envisaged for use with any suitable means of conveyance, such as wireline, coiled tubing, logging while drilling (LWD), and so forth. Further, information regarding the environment, such as the Sigma of the formation. Sigma of the mud, density, borehole size, and slowdown length, can be gained using additional equipment as further discussed below.

Figure 3:
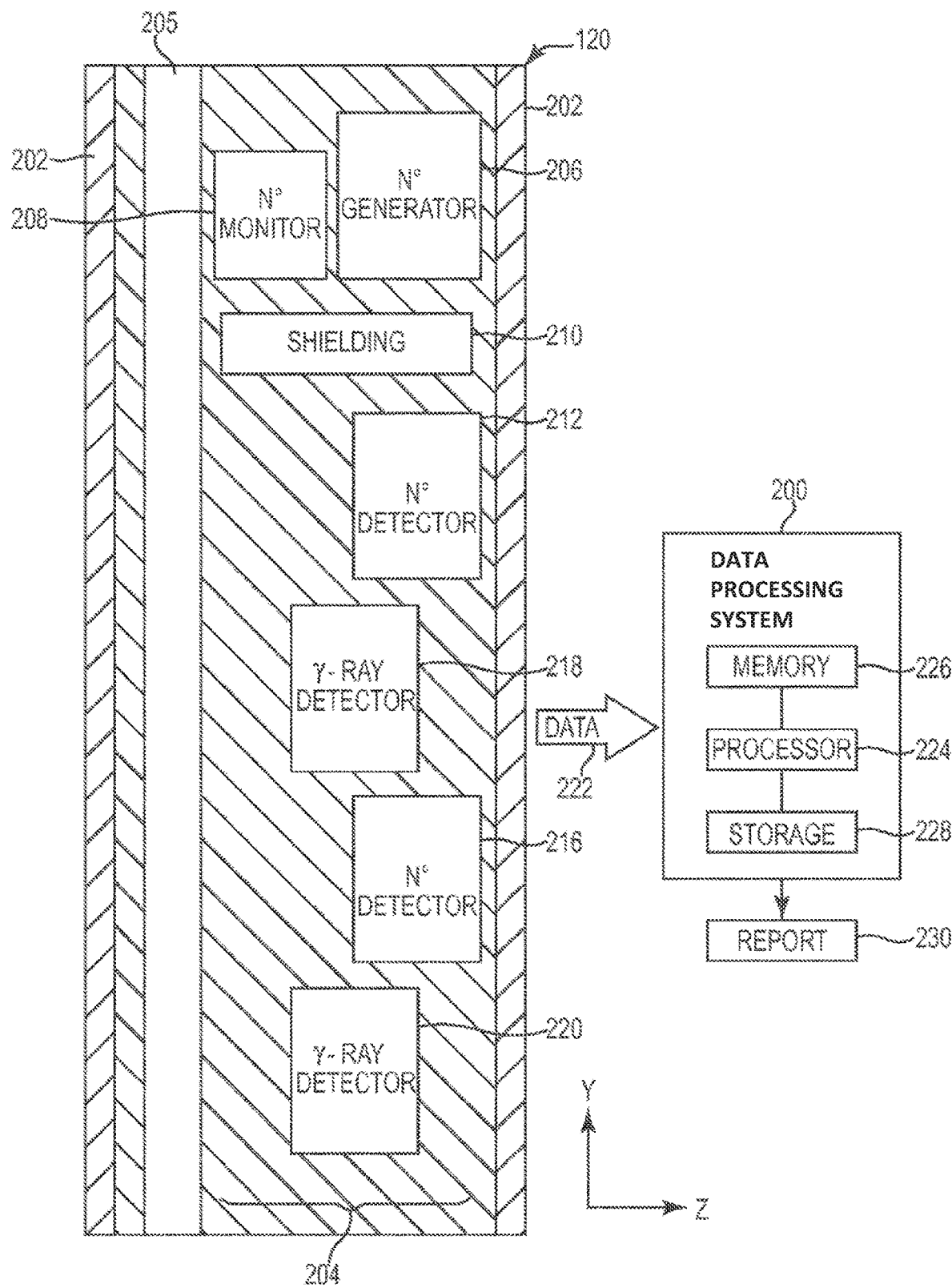
FIG. 3 is a schematic diagram of an exemplary spectroscopy logging tool in accordance with an embodiment of the present disclosure, which can be part of the wellsite system of FIG. 1.

FIG. 3 is a schematic illustration of an exemplary spectroscopic logging tool, which can be part of an LWD module 120 of the bottomhole assembly 100 of FIG. 1. The LWD module 120 can be associated with data processing circuitry 200. Although the LWD module 120 and the data processing circuitry 200 are depicted as independent elements in FIG. 3, one can appreciate that the data processing circuitry 200 can be implemented entirely within the LWD module 120, at the surface remote from the LWD module 120, or partially within the LWD module 120 and partially at the surface. By way of example, the LWD module 120 can represent a model of the EcoScope™ tool by Schlumberger Technology Corporation.

The chassis 204 of the LWD module 120 can house a variety of components and configurations for emitting and detecting radiation to obtain a spectroscopy measurement. For example, a neutron source 206 can serve as a neutron source that emits neutrons of at least 2 MeV to create gamma rays through inelastic scattering with formation elements. By way of example, the neutron source 206 can be an electronic neutron source, such as a Minitron™ device commercially available from Schlumberger Technology Corporation, which can produce pulses of neutrons through deuteron-deuteron (d-D), deuteron-triton (d-T), triton-triton (t-T) or other suitable reactions. Thus, the neutron source 206 can emit neutrons around 2 MeV or 14 MeV, for example, or neutrons with a broad range of energies such as those obtained from continuous sources of neutrons such as 241AmBe or 252Cf radioisotope sources.

In some embodiments, the chassis 204 can further house a neutron monitor 208 that can be configured to monitor the neutron emissions from the neutron source 206. By way of example, the neutron monitor 208 can be a plastic scintillator and photomultiplier that primarily detects unscattered neutrons directly emitted from the neutron source 206, and thus can provide a count rate signal proportional to the neutron output rate from the rate of neutron output of the neutron source 206. Illustrative but non-limiting examples of suitable neutron monitors are described in U.S. Pat. No. 6,884,994, which patent is incorporated by reference herein.

The chassis 204 can further include neutron shielding 210 (such as tungsten, lead or boron,) that prevents neutrons emitted by the neutron generator 206 from passing internally through the LWD module 120 toward various radiation-detecting components on the other side of the shielding 210. Suitable tungsten shielding material is available commercially from PLANSEE USA LLC of 115 Constitution Boulevard. Franklin Mass. 020038. Suitable boron shielding can be obtained from a variety of sources and can include boron in several different forms such as metallic boron, B4C, BN and others. In some embodiments, boron enriched with a 10B isotope is used and is commercially available from Ceradyne, P.O. Box 798, Quapaw Okla. 74363.

The chassis 204 can further include one or more near or collocated neutron detectors 212 (such as a near thermal neutron detector and a near epithermal neutron detector), as well as one or more additional far or collocated neutron detectors 216 (such as a far thermal neutron detector and a far epithermal neutron detector). The far neutron detector(s) 216 arm spaced farther from the neutron generator 206 than the near neutron detector(s) 212. Neutron detectors are commercially available from GE Reuter Stokes of Twinsburg Ohio and Schlumberger Technology Corporation of Houston, Tex.

A short spacing (SS) gamma ray detector 218, such as a detector using NaI, LaBr, or GSO, can be located between the near neutron detector(s) 212 and the far neutron detector (s) 216. A long spacing (LS) gamma ray detector 220 can be located beyond the far neutron detector(s) 216, at a spacing farther from the neutron generator 206 than the gamma ray detector 218. Gamma ray detectors are commercially available from Saint-Gobain Crystals of 17900 Great Lakes Parkway, Hiram Ohio 44234-9681. Alternative embodiments of the LWD module 120 can include more or fewer of such radiation detectors, but generally can include at least one gamma ray detector. The neutron detectors 212, 216 can be any suitable neutron detectors, such as 3He neutron detectors. To detect primarily epithermal neutrons, epithermal neutron detectors can be surrounded by thermal neutron shielding, while thermal neutron detectors are not.

The gamma ray detectors 218 and/or 220 can be scintillation detectors surrounded by neutron shielding. The neutron shielding can include, for example, 6Li, such as lithium carbonate ($Li_2CO_3$), which can substantially shield the gamma ray detectors 218 and/or 220 from thermal neutrons without producing thermal neutron capture gamma rays. The gamma ray detectors 218 and 220 can detect inelastic gamma rays generated when fast neutrons from the neutron generator 206 inelastically scatter off certain elements of a surrounding formation.

The count rates and energy spectra of gamma rays from the gamma ray detectors 218 and 220 and count rates of neutrons from the neutron detectors 212, 216 can be received as data 222 by a data processing system 200. The data processing system 200, which can be part of other noted components or structure or separate components or structure, provides means for receiving the data 222 and performing certain steps or processing to determine or estimate one or more properties of the surrounding formation, such as formation mineralogy and other properties disclosed herein. The data processing system 200 can include a processor 224 and memory 226 and/or storage 228 that cooperate to perform steps or instructions to carry out the disclosed objectives. Techniques disclosed herein can be carried out by the processor 224 and/or other data processing circuitry based on corresponding instructions executable by the processor 224. Such instructions can be stored using any suitable article of manufacture, which can include one or more tangible, computer-readable media to at least collectively store these instructions. The article of manufacture can include, for example, the memory 226 and/or the nonvolatile storage 228. The memory 226 and the nonvolatile storage 228 can include any suitable articles of manufacture for storing data and executable instructions, such as random-access memory, read-only memory, rewriteable flash memory, hard drives, and optical disks. The memory 226 and storage 228 are collectively referred to herein as data storage.

The LWD module 120 can transmit the data 222 to the data processing system 200 via, for example, internal connections within the tool, a telemetry system communication uplink, and/or a communication cable. The data processing system 200 can determine or estimate one or more properties of the surrounding formation. By way of example, such properties can include the relative spectral yields of the capture gamma rays for atomic elements or the concentrations of atomic elements of the formation. The data processing system 200 can also apply the elemental concentrations of the formation as derived from the data 222 (or other data pertaining thereto) as input to a trained machine learning model to determine estimates of mineral component concentrations of the formation and possibly other formation properties based thereon. The data processing system 200 can further output such information in a log or report 230 to aid in evaluation of the formation. The log or report 230 can be stored in memory or storage for later further processing by the system 200 or by other systems or circuitry, or can be provided to an operator via one or more output devices, such as an electronic display.

In embodiments, the LWD module 120 can be configured to perform neutron-capture spectroscopy where neutrons generated by the neutron source 206 interact with elemental nuclei in the formation surrounding the logging tool and produce prompt (inelastic) and capture gamma radiation in a local volume surrounding the logging tools. The elemental nuclei can be located in the formation rock, the formation pore space, the borehole fluids, or in the tool itself. The characteristic gamma-ray spectrum associated with each element can be recognized, and the total measured energy spectrum can be analyzed to derive the relative contribution of each element. Often, but not always, the elements of interest are those located in the formation.

According to one embodiment, the data obtained by the spectroscopic logging tool can be used to determine an estimate of mineral component concentrations and possibly other formation properties for part of the near-borehole formation that is investigated by the spectroscopic logging tool. According to one aspect, such determination or determinations may be made using advanced machine learning tools which build one or more predictive machine learning models to estimate mineral component concentrations.

In embodiments, the predictive machine learning model(s) include at least one artificial neural network (ANN) or other neural network that is configured and trained to predict mineral component concentrations from the data obtained by the spectroscopic logging tool. An artificial neural network (ANN) is a computational system that is inspired by, but not identical to biological neural networks that constitute animal brains. Such systems are trained (or "learn") to perform specific tasks by considering examples. For example, in image recognition, an ANN might learn to identify images containing cats using example images that have been manually labeled as "cat" or "no cat". The resulting trained ANN can then be used to identify other images containing cats. It can do this without any prior knowledge of cats, for example, that they have fur, whiskers and cat-like faces.

An ANN employs a collection of connected units or nodes called artificial neurons or neurons, which loosely model the neurons in a biological brain. Each connection, like the synapses in a biological brain, can transmit a signal to other artificial neurons. An artificial neuron that receives a signal can process it and signal one or more artificial neurons connected to it. In an ANN, the signal at a connection is a real number or integer, and the output of each artificial neuron is computed by some non-linear function of the sum of its inputs. The connections are called edges. The edges typically have weights that increase or decrease the strength of the respective signals for the connections. The weights are adjusted as learning proceeds. Artificial neurons can have a threshold such that a signal is sent only when the signal crosses the threshold.

Typically, the artificial neurons of the ANN are organized as layers that each includes one or more artificial neurons, where the layers include an input layer (first layer), an output layer (last layer) and one or more hidden layers between the input layer and the output layer. The input layer receives external data. The output layer produces result data. In a feedforward neural network, the connections between the artificial neurons do not form a cycle. The information moves in only one direction, forward, from the input layer to the hidden layer(s), if any, and to the output layer. There are no cycle or loops in the network. In this case, the artificial neurons of a given hidden layer can connect to artificial neurons of the immediately preceding and immediately following layers.

The ANN has hyperparameters, which are inherent parameters whose values are set before the learning process begins. Typical examples of hyperparameters include learning rate, the number of layers and number of neurons per layer. The learning or training process is the adaptation of the ANN to better handle a task by considering labeled observations as inputs to the ANN. The learning or training process typically involves adjusting the weights (and possibly thresholds) of the ANN to improve the accuracy of the result data. This is typically accomplished by minimizing a cost function that represents a measure of the accuracy of the result data of the ANN with respect to a given labeled observation as input. The learning rate typically defines the size of the corrective step that the ANN will take in adjusting the weights (and possibly thresholds) of the ANN.

The learning or training process of the ANN can employ supervised learning. In supervised learning, the learning or training process uses a set of paired observations and desired outputs or labels, and the learning task is for the ANN to produce the desired output or label for the paired observation taken as input to the ANN. In this case, the cost function is related to eliminating incorrect deductions. A commonly used cost is the mean-squared error, which tries to minimize the average squared error between the output of the ANN and the desired output or label.

Alternatively, the learning or training process of the ANN can employ unsupervised learning with no pre-existing labels and with a minimum of human supervision.

In embodiments, the predictive machine learning model(s) of the methods and systems as described herein employ an autoencoder-type ANN (or autoencoder). To illustrate the methods and systems, a dataset(s) containing the measured concentrations of atomic elements will be represented by E, a dataset(s) containing the measured mineral component concentrations will be represented by M, a dataset(s) containing the derived mineral component concentrations will be represented by M', and a dataset(s) containing the derived reconstructed concentrations of atomic elements will be represented by E'. The autoencoder is configured and trained to estimate (i) mineral component concentrations M' and (ii) reconstructed elemental concentrations E' based on measured elemental concentrations E provided as input.

Figure 4:
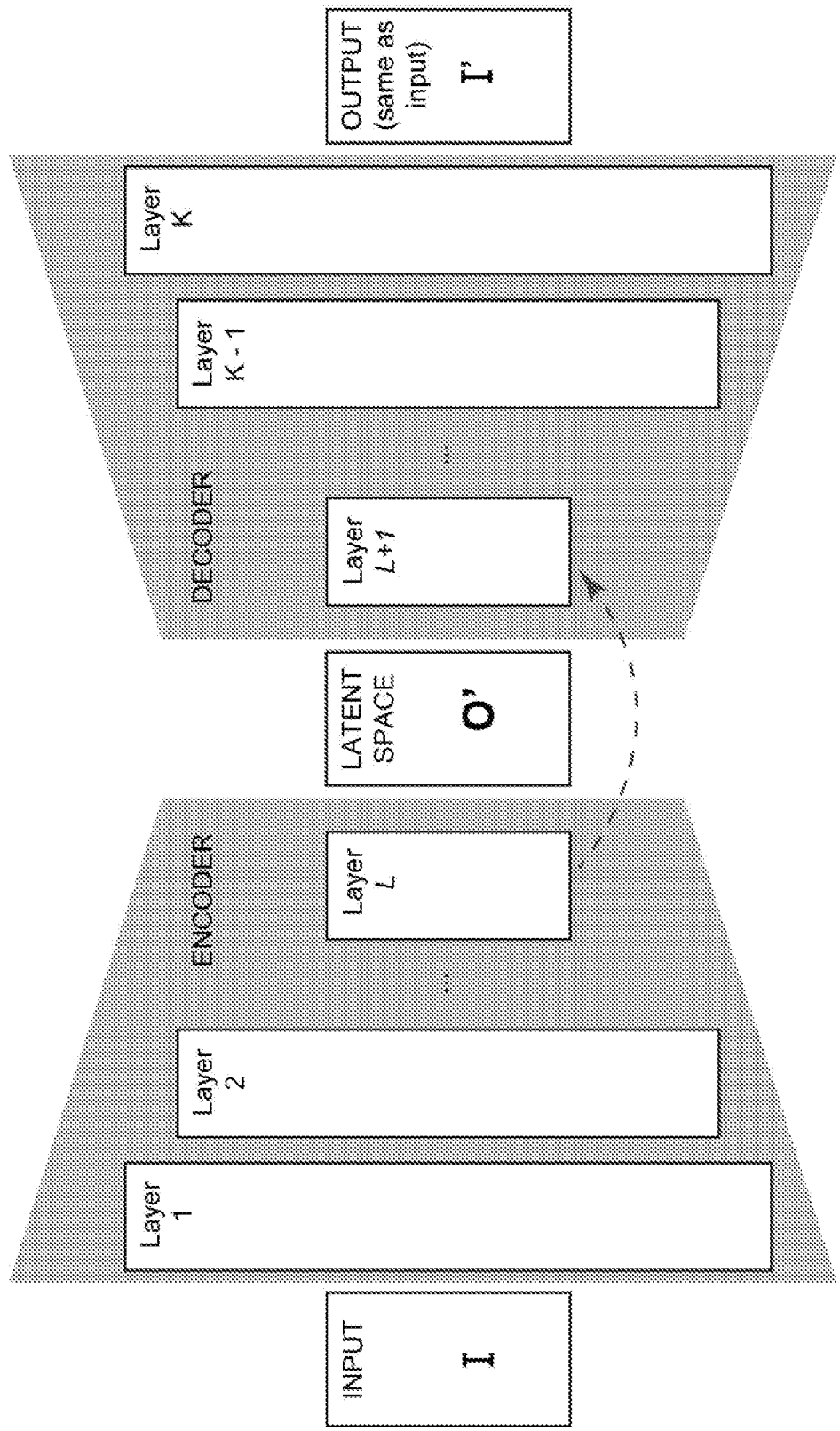
FIG. 4 is a schematic diagram of an autoencoder, which has an encoder part with L layers, a latent space representation O, and a decoder part with (K-L) layers.

FIG. 4 illustrates an architecture of an example autoencoder. An autoencoder is a type of ANN that learns efficient data codings by unsupervised learning. The aim of an autoencoder is to learn a representation (encoding) for a set of data, typically for dimensionality reduction, by training the artificial neural network to ignore signal "noise." Along with the reduction side, a reconstructing side is learnt, where the autoencoder tries to generate from the reduced encoding a representation as close as possible to its original input, hence its name.

Architecturally, the simplest form of an autoencoder is a feedforward, non-recurrent neural network having an input layer, an output layer and one or more hidden layers connecting them. The output layer has the purpose of reconstructing the inputs. Therefore, autoencoders are unsupervised learning models.

Autoencoders are typically logically organized as two parts: an encoder that extracts relevant information from the input (also referred to as features) and maps it into a latent space representation, and a decoder that maps the latent space representation back into the original input as an output. Autoencoders are commonly symmetric about the latent space, and commonly either the encoder or decoder is individually used for subsequent applications.

Autoencoders may be trained as follows, with reference to FIG. 4: For each input I, the artificial neural network does a feed-forward pass with activation through (hidden) layers, resulting in an output I'. The mean square error between the derived values of the output I' and the values of the input I is back-propagated to update the weights in each layer of the network. Autoencoders have multiple applications including de-noising, data compression, dimensionality reduction, and significant feature identification.

In embodiments of the present disclosure, the objective is to learn and apply a simultaneous mapping of mineral concentrations M from elemental concentrations E (the encoder) and of elemental concentrations E' from mineral concentrations M (the decoder). The motivation for using the autoencoder architecture is to simultaneously minimize distortion loss between measured elements E and predicted elements E' as well as the distortion loss in the latent space representation between the measured minerals M and predicted minerals M'. This is useful since the problem of estimating mineral concentrations from elemental concentrations is ill-conditioned in the sense that the number of possible minerals to be identified is much larger than the number of elements available as constraints (size of matrix M>size of matrix E). Moreover, certain different minerals can have identical or nearly identical chemical compositions. As two or more vectors representing the chemical compositions of two or more minerals become increasingly alike, the condition number of the matrix comprising the vectors becomes large, making these minerals difficult to resolve. In the case that two minerals have identical chemical compositions, they are impossible to resolve without other useful data. Furthermore, it is possible that two or more sets of certain different mineral concentrations in two or more geological rock formations, may have the identical bulk elemental concentrations, even in the case where the number of minerals in the geological rock formation(s) of interest is less than the number of elements available to describe those minerals and where those minerals have distinct chemical compositions. In other words, one or more solutions to M can be equally probable from one set of measurable bulk elemental concentrations E. Reconstructing elemental concentrations E' from predicted mineral concentrations M' in some sense tries to eliminate the multiple mineral solutions that are possible. In addition, the reconstruction error in the elemental concentrations serves as a flag for erroneous predictions.

In other embodiments, the methods and systems can be optionally used only to learn and apply the mapping from elemental concentrations E (input) to mineral concentrations M (latent space representation) in the encoder, ignoring the mapping from mineral concentrations M (latent space representation) to reconstructed elemental concentrations E' (output) in the decoder. This may be accomplished for example by setting the number of layers in the decoder equal to zero (i.e., K layers equal to zero in FIG. 4).

In the aforementioned description, the latent space representation can be used explicitly as an input to the decoder. In yet other embodiments, the output of the final hidden layer L in the encoder may be used directly as an input to the first layer L+1 of the decoder (indicated by the dashed arrow in FIG. 4).

Input Data

To train the autoencoder, the input data comprises measured concentrations of atomic elements E and measured mineral component concentrations M of a set of formation samples. The measured elemental concentrations E can represent concentrations of a number of atomic elements commonly found in reservoir rocks, such as one or more atomic elements selected from the group consisting of Si, Al, Ca, Mg, K, Fe, S. The measured mineral component concentrations M can represent concentrations of a number of mineral components commonly found in reservoir rocks, such as one or more mineral components selected from the group consisting of quartz, albite, anorthite, orthoclase, plagioclase, kaolinite, illite, smectite, chlorite, muscovite, biotite, calcite, dolomite, siderite, ankerite, pyrite, anhydrite, salt, and coal. The data comprising E and M must be accurate within accepted uncertainties to learn an accurate mapping between the two. Once trained, the models represented by the encoder part of the autoencoder can be used predictively to derive estimates of unknown values of mineral concentrations M' for unknown formation samples only with some knowledge from measurement or otherwise of the elemental concentrations E of said unknown formation samples.

In certain embodiments, the data sets comprising E and M for the training process can be determined using well-known laboratory techniques. An example is the determination of mineral concentrations using X-ray diffraction (XRD) or infrared spectroscopy (IR) measurements. Another example is the determination of elemental concentrations using X-ray fluorescence spectroscopy (XRF), mass spectrometry, neutron activation, and the like. In other embodiments, these data can be synthetically constructed for a limited number of minerals and their associated elements. The addition of synthetic data can be used, for example, to expand the range of data and to increase robustness of the derived mapping functions. Optionally, as described below, the uncertainties on the input data may be used in the model to benefit the estimation on uncertainties on the output data.

Model Architecture

Figure 5:
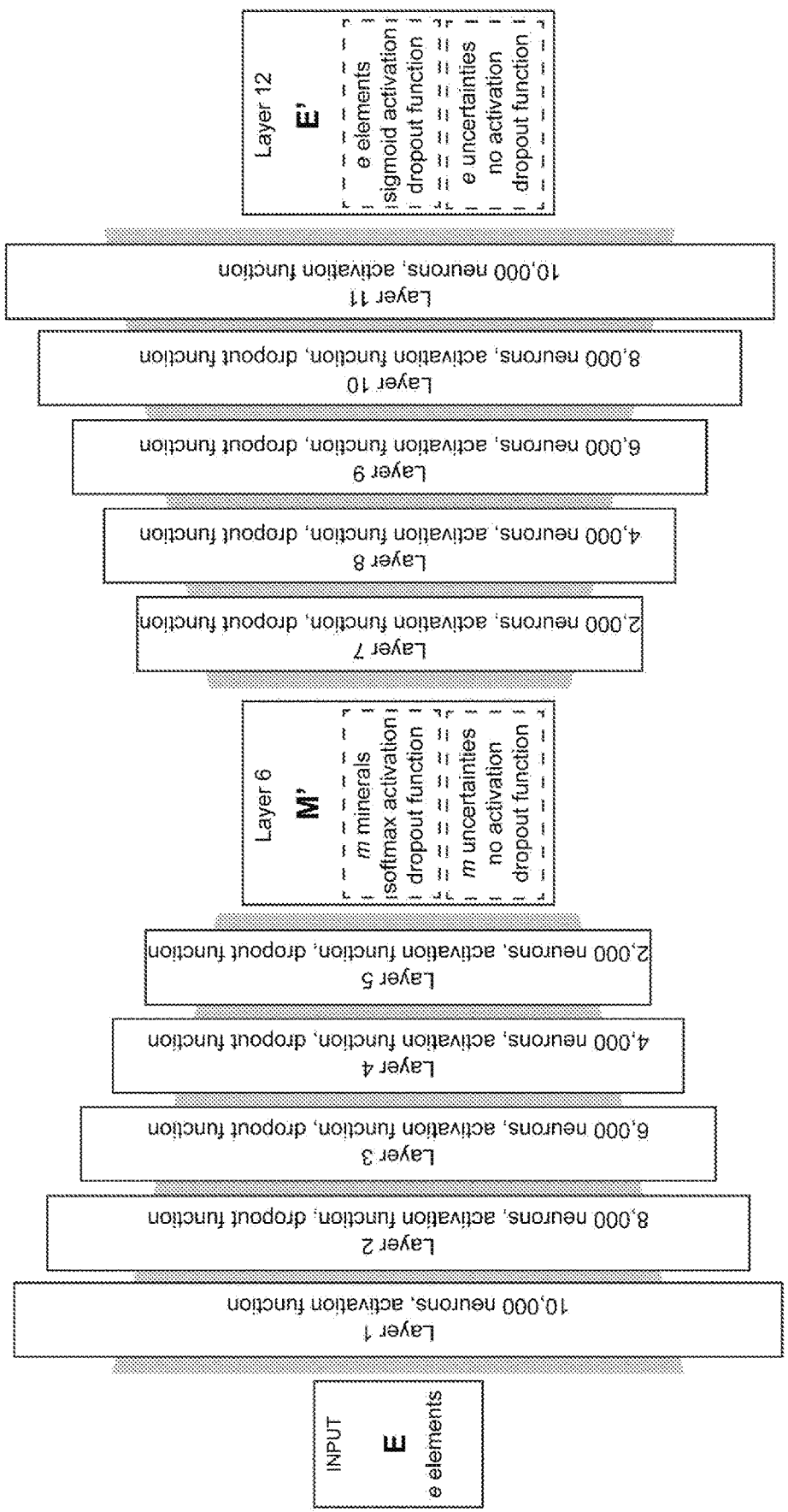
FIG. 5 is a schematic diagram of an autoencoder according to an embodiment the present disclosure, which has an encoder part with 5 layers, a latent space representation M', and a decoder part with 5 layers.

FIG. 5 illustrates one embodiment of an autoencoder architecture as may be used for the methods and systems of the present disclosure. The autoencoder of FIG. 5 is an artificial neural network (ANN) that takes the elemental concentrations E as values for the input, which then pass through a series of hidden layers to map to output nodes as values in the latent space representation (e.g., predicted mineralogy M' comprising m number of minerals/nodes) and in the output space (e.g., reconstructed elemental concentrations E' comprising e number of elements/nodes), wherein each output node may optionally include an associated estimate of the uncertainty on the prediction of the value of the outputs. A layer here is defined as a series concatenation of a weight matrix (that performs a linear transformation), an elementwise activation function (which introduces non-linearities), and a dropout function. The activation function of a node or "neuron" defines the output of that node given an input or set of inputs. The dropout function is not required but is beneficial for estimating aleatoric and epistemic uncertainties in the autoencoder. In some embodiments, the dropout function is used; in other embodiments, the dropout function is not used. Connections to the nodes of a layer that provide an input or set of inputs to the nodes of the layer can be characterized by weights encoded by the weight matrix. Each node can utilize an associated activation function (and possibly an associated dropout function) to generate an output dependent on the data received on each input connection and the associated weight of the input connection. The layers of the ANN are adaptive in that the connection weights of the layers can be adjusted to change the response of the ANN to a particular input or class of inputs.

In one or more embodiments, the latent space layer M' (which includes the latent space representation of mineral concentrations produced by the encoder part of the autoencoder) can use an optional activation function to ensure a sum-to-one constraint followed by a lambda transformation that multiplies the output by 100. In other embodiments, no such sum-to-one constraint is used for the same output of the latent space layer M'. In this case, the output may be beneficial, for example, to indicate the presence of missing minerals not included in the mineralogy output.

In one or more embodiments, the output layer E' can use an optional activation function to ensure non-negativity of the reconstructed output values.

In one or more embodiments, once training of the mapping function from E to M and E' is complete, predictions and uncertainties on the outputs can be obtained via multiple feed-forwards while ensuring that dropout segments remain active.

As described above, in some embodiments, the methods and systems can optionally be used only to learn and apply the mapping from elemental concentrations E (input) to mineral concentrations M (latent space representation) in the encoder. In yet other embodiments, the autoencoder architecture can ignore the explicit mapping from the mineral concentrations in the latent space representation and instead directly map from the elemental concentrations E (input) to the reconstructed elemental concentrations E' (output). The mineral concentrations (latent space representation) may be derivable as one of the outputs of the intermediate layers of the neural network.

In other embodiments, the autoencoder architecture uses the concept of a stacked encoder. It involves a bottom-up approach where the layers of the final ANN are trained in an additive, unsupervised manner, followed by a supervised learning phase for the topmost layer, while the bottom layers remain agnostic with respect to the final learning task.

Output Data

In embodiments, the latent space representation of the autoencoder are latent space variables comprising an estimate of the mineral concentration(s) and optionally their associated uncertainty(ies). The output from the autoencoder are the output variables comprising reconstructed concentrations of atomic elements and optionally their associated uncertainty(ies).

Cost Function

The cost function employed by the autoencoder can be based on mean square error (MSE), although it can be easily modified to include the mean absolute error or minimization of the maximum error. The uncertainty in mineral and elemental concentration predictions represents both the data and model uncertainty. This uncertainty can be captured in a heteroscedastic cost function generalized as follows:

$$\sum_{i=0}^{m} \frac{(M_i - \hat{M}_i)^2}{\sigma_{m_j}^2} + \log(\sigma_{m_i}) + \sum_{i=0}^{e} \frac{(E_i - \hat{E}_i)^2}{\sigma_{E_i}^2} + \log(\sigma_{E_i}) \quad \text{(Eq. 1)}$$

Note that the first terms following each summation sign in the cost function of Eqn. (1) serves to minimize the mean square error between mineral input and mineral predictions in the latent space representation and the elemental input and elemental reconstructions obtained at the output of the autoencoder. The denominator $\sigma_{m_i}$ and $\sigma_{E_i}$ represents the uncertainty in the estimated mineral and element outputs. The second terms $\log(\sigma_{m_i})$ and $\log(\sigma_{E_i})$ in the cost function of Eqn. (1) serve as regularization functionals, the inclusion of which attempts to find a unique solution that balances model robustness and accuracy.

In other embodiments, the cost function employed by the autoencoder can be the sum of the heteroscedastic losses with cross-entropy, or a polynomial functional form for the regularization functional, or a mean absolute error for the measure of accuracy, or the like.

Activation Functions

Traditionally, an ANN employs well-known sigmoid and tan h activation functions in the hidden layers to introduce non-linearities. FIGS. 6A and 6B graphically illustrate the sigmoid and tan h activation functions, respectively. The magnitude of the gradient (derivative) for both functions never exceeds one. This implies that, for deep learning methods wherein many hidden layers are used successively, the gradients will become diminutive during backpropagation and the weights for the nodes in the hidden layers will not change in value. This is called the vanishing gradient problem. Additionally, for normalized data, the activations tend to remain very close to zero. This implies that the activations lie within the linear regime of the sigmoid/tanh function and, as such, the whole network starts behaving practically linearly. To compensate for the above-mentioned problems, the rectified linear unit (ReLU) activation function was introduced (e.g., Krizhevsky, A., Sutskever, I. and Hinton, G. E., 2012, "ImageNet classification with deep convolutional neural networks," $31^{st}$ *Conference on Neural Information Processing Systems*, Lake Tahoe, Nevada, USA, 3-8 December). FIG. 6C graphically illustrates the ReLU activation function. Apart from being easy to calculate, zero-centered activations are in the non-linear regime of the function. It introduces sparsity in the activation pattern which forces the ANN to learn highly distinguishable features. However, large number of negative activations can again lead to the vanishing gradient problem. The Leaky ReLU activation function avoids this problem by incorporating a small positive gradient (coefficient of leakage) to the ReLU function. FIG. 6D graphically illustrates the Leaky ReLU activation function. The gradient is typically assigned a fixed value, equal to 0.01. In one or more embodiments of the method, the ANN uses the parametric ReLU (PReLU) activation function, which parametrizes the value of the gradient of the Leaky ReLU function as a learnable parameter (e.g., He, K., Zhang, X., Ren, S. and Sun, J., 2015, "Delving deep into rectifiers: Surpassing human-level performance on ImageNet classification. *IEEE International Conference on Computer Vision (ICCV)*, 11-18 December).

In one or more embodiments, the latent space representation of the autoencoder includes estimated mineral concentrations M' together with a softmax activation function, $S(m_i)=\exp(m_i)/\Sigma j(\exp(m_i))$, which normalizes the output such that the sum of the components of the output (the concentration of the m number of minerals) is one. Additionally, the gradient of the function can be easily calculated during backpropagation.

In one or more embodiments, the autoencoder can utilize a lambda transformation to multiply the output by 100, such that it sums to 100. In one or more embodiments, the layer comprising the output of the reconstructed elemental concentrations E' can use a sigmoid activation function, to ensure non-negativity of the said output values.

Uncertainty in the Latent Space Representation (Minerals) and Outputs (Elements)

There are many ways to incorporate uncertainty into the autoencoder. In one or more embodiments, a dropout function is used to derive the estimate of uncertainty, for example using concrete dropout approach as described in Gal, Y., Heron, J. and Kendall, A., 2017, "Concrete Dropout." 31st Conference on Neural Information Processing Systems, Long Beach, California, USA, 4-9 December. Traditionally, dropout functions have been used to prevent overfitting of a model. Dropout functions work by randomly switching off nodes or neurons based on a certain Bernoulli parameter during the training of the ANN. This forces the nodes or neurons to not co-depend on each other and forces them to learn unique, distinguishable features. Traditional dropout segments remain active in the training phase but not in the testing phase. During the testing phase, the outputs are essentially multiplied by a factor dependent on dropout's Bernoulli parameter to keep the expectation of the activations the same as that of the training phase. In a recent paper by Gal, Y. and Ghahramani, Z., 2016, "Dropout as a Bayesian approximation: Representing model uncertainty in deep learning," Proceedings of the 33rd International Conference on Machine Learning, New York, New York, USA, 19-24 June, another possible application of dropout functions is described that estimates uncertainties by keeping them activated during testing phase. The claim is that such a network is approximately equivalent to a deep Gaussian process. A drawback is that the value of the Bernoulli parameter for each dropout segment must be manually set, i.e., it is a hyperparameter. Optimizing the hyperparameter requires grid-search and for heavy neural networks, and the computational cost can be prohibitively high. Concrete dropout segments replace dropout's discrete Bernoulli distribution with its continuous relaxation, i.e., the concrete distribution relaxation. This relaxation allows re-parametrization of the Bernoulli distribution and essentially makes the neural network parameters learnable. In other embodiments, an ensemble is instead used to determine the estimate of uncertainty on the outputs (e.g., Lakshminarayanan, B., Pritzel, A. and Blundell. C., 2017, "Simple and scalable predictive uncertainty estimation using deep ensembles," $31^{st}$ *Conference on Neural Information Processing Systems*, Long Beach, California, USA, 4-9 December).

In embodiments, randomness in the autoencoder can be introduced by training ensemble data representing different samples of the original input data. The training ensemble data could represent uncertainties on the original input data as captured by, for example, Gaussian or Poisson distributions. Missing input data can be represented, for example, by large uncertainties. The uncertainties can be different for different input data as well as for the same input data depending upon its magnitude. Data of this type is commonly referred to as data having heteroscedasticity or different fidelities. Estimates of uncertainty can be derived from the values of the outputs from multiple ensembles of the model, for example from the mean and standard deviation of the output value distributions.

Other Embodiments

The above descriptions and figures illustrate specific embodiments of autoencoder architectures as may be conceived to map from an input data to the latent space data (encoder) and from the latent space data to an output data (decoder). In the above, the input data comprises a set of elemental concentrations representing the solid rock of a part or sample of a formation, as derived from a measurement performed on the formation part or sample. In other embodiments, the input data for the training process as well as for the trained autoencoder need not be the concentrations of atomic elements themselves, but any other data representation pertaining to those concentrations. For example, such input data could be the directly measured X-ray spectrum of a formation part or sample because in this spectrum is contained the information pertaining to the identification (X-ray photon energy) and concentration (X-ray photon counts) of one or more elements in said formation. Similarly, the input data could be the directly measured gamma-ray spectrum of a formation sample because in this spectrum is contained the information pertaining to the identification (gamma-ray energy) and concentration (gamma-ray counts) of one or more elements in said formation. Note that the present disclosure is not limited to those inputs explicitly disclosed herein and can include other inputs.

Determining Beneficial Estimates of Formation Properties

The methods and systems of the present disclosure provide a novel means to derive a beneficial estimate of the mineral concentrations in a part or sample of rock formation using an ANN mapping function. In embodiments, the ANN mapping function can be based on the encoder part of a trained autoencoder.

In one or more embodiments, the estimated mineral concentrations produced by the ANN mapping function can be used to determine estimates of other formation properties. This is practically beneficial in the practice of performing downhole logging measurements within a borehole that traverses a subterranean rock formation, as will become clear in the following subject description. One example of a beneficial formation property is matrix density. Wherein the solid rock comprises only minerals, the computation of the formation matrix density is expressed as in Eq. 2:

$$\frac{1}{\rho_{ma}} = \frac{M_1}{\rho_{g,1}} + \frac{M_2}{\rho_{g,2}} + \ldots + \frac{M_i}{\rho_{g,i}} = \sum_{i=1} \frac{M_i}{\rho_{g,i}} \quad \text{(Eq. 2)}$$

In this case, the formation matrix density $\rho_{ma}$ is computed as the sum of the individual mineral mass fractions $M_i$ each divided by their respective mineral grain densities $\rho_{g,i}$. The summation is performed over all minerals i and, in general, the mineral mass concentrations are prescribed such that their sum is normalized to one, i.e., $\Sigma M_i = 1$. For minerals that are common in earth and other formation samples, their mineral grain densities are well known and do not need to be derived. In this case, the mineral mass fractions $M_i$ are derived from the ANN mapping function from elements to minerals. When the calculation is performed in connection with measurements of formation samples obtained from a borehole or from measurements performed by a logging device in a borehole, the calculation can provide a continuous estimate of formation matrix density as a function of depth along the borehole.

Furthermore, the relationship established in Eq. 2 may be used to compute a beneficial estimate of the formation porosity, by combining the formation matrix density estimation with measurements of formation bulk density in accordance with Eq. 3:

$$\phi = \frac{\rho_{ma} - \rho_b}{\rho_{ma} - \rho_f} \quad \text{(Eq. 3)}$$

In this case, $\phi$ is formation porosity, $\rho_b$ is bulk density measured, for example, by a density logging sonde; and $\rho_f$ is fluid density. When the calculation is performed in connection with measurements of formation samples obtained from a borehole or from measurements performed by a logging device in a borehole, the calculation can provide a continuous estimate of formation porosity as a function of depth along the borehole.

Another example is the computation of formation matrix Sigma, i.e., the macroscopic thermal-neutron capture cross section $\Sigma$. This computation is expressed as in Eq. 4:

$$\Sigma_{ma} = V_1 \cdot \Sigma_1 + V_2 \cdot \Sigma_2 + \ldots + V_i \cdot \Sigma_i = \quad \text{(Eq. 4)}$$
$$\rho_{ma}\left(\frac{M_1}{\rho_{g,1}}\Sigma_1 + \frac{M_2}{\rho_{g,2}}\Sigma_2 + \ldots + \frac{M_i}{\rho_{g,i}}\Sigma_i\right)$$

In this case, $V_i$ and $\Sigma_i$ are, respectively, the individual volume fractions and Sigma values of each mineral i and, in general, the mineral volume fractions prescribed such that their sum is normalized to one, i.e., $\Sigma V_i = 1$. As illustrated, the computation may be performed in analogous fashion using mineral mass fractions $M_i$. In this case, the mineral mass fractions $M_i$ are derived from the ANN mapping function. When the calculation is performed in connection with measurements of formation samples obtained from a borehole or from measurements performed by a logging device in a borehole, the calculation can provide a continuous estimate of formation matrix Sigma as a function of depth along the borehole.

Furthermore, the relationship illustrated in Eq. 4 may be used to compute a beneficial estimate of the formation water saturation, by combining the formation matrix Sigma estimation with measurements of formation bulk Sigma in accordance with Eq. 5:

$$S_w = \frac{(\Sigma_b - \Sigma_{ma}) + \phi(\Sigma_{ma} - \Sigma_{hc})}{\phi(\Sigma_w - \Sigma_{hc})} \quad \text{(Eq. 5)}$$

where, $S_w$ is formation water saturation; $\Sigma_b$, $\Sigma_{ma}$, $\Sigma_{hc}$, and $\Sigma_w$ are the Sigma values for the bulk formation, matrix, hydrocarbon (oil or gas), and water in the formation, respectively; and $\phi$ is formation porosity as introduced above. When the calculation is performed in connection with measurements of formation samples obtained from a borehole or from measurements performed by a logging device in a borehole, the calculation can provide a continuous estimate of water saturation as a function of depth along the borehole. These exemplary applications are well known to those skilled in the art.

Other applications for the determination of formation properties derived from an estimate of formation mineral concentrations are well known to those skilled in the art and the benefit of deriving an estimate of mineral concentrations in formation samples is obviously not limited only to those examples explicitly described in the present disclosure. The benefit of our method is in that a more accurate determination of mineral concentrations can provide a more accurate estimate of formation properties derived therefrom. The beneficial matrix and formation properties that may be derived from our method are not limited to those explicitly described in the subject disclosure.

Figure 7:
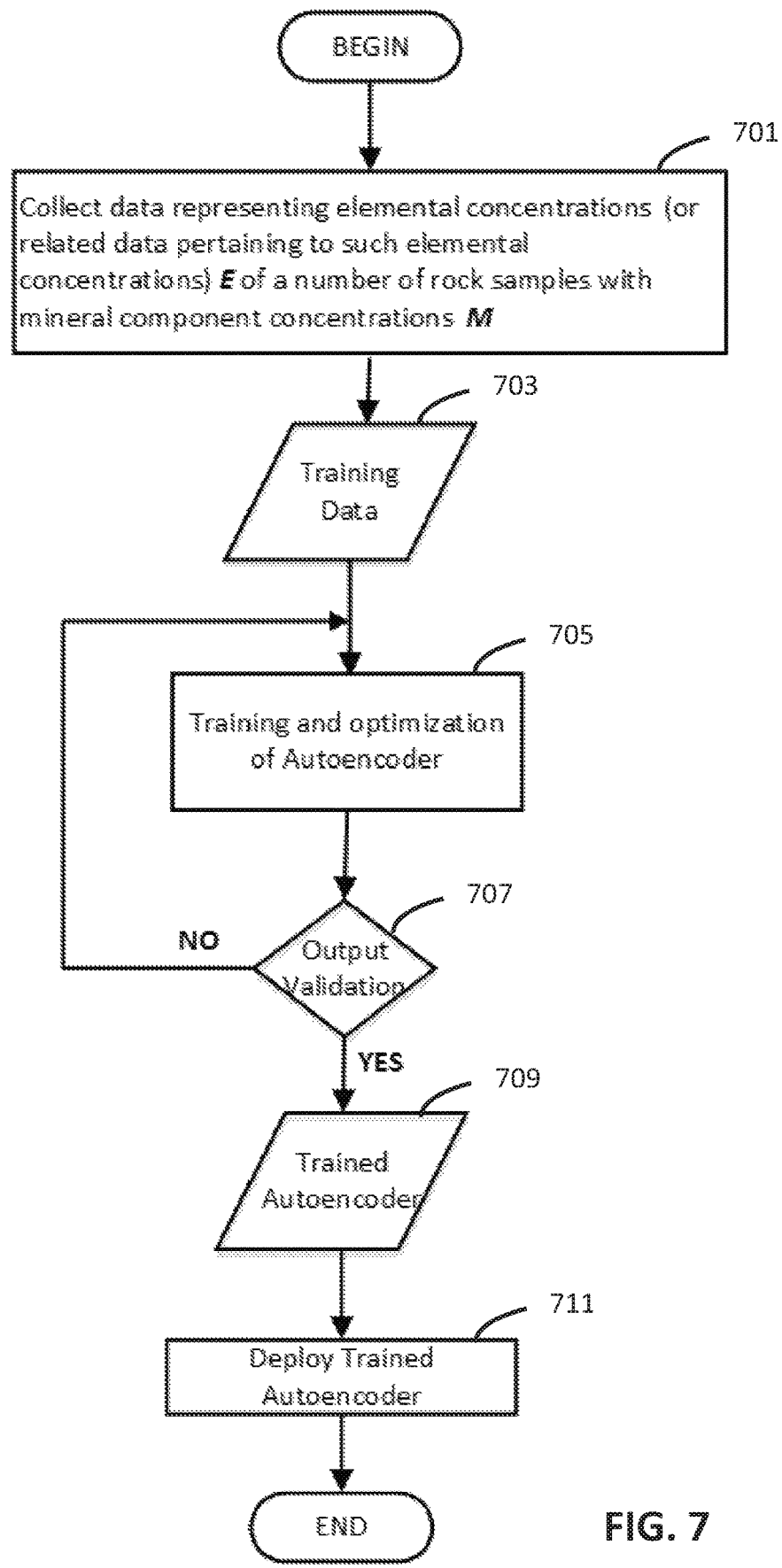
FIG. 7 is a flowchart illustrating an exemplary workflow for training an autoencoder in accordance with an embodiment of the present disclosure.

An example workflow regarding the building and training of an autoencoder for estimating formation mineral concentrations is illustrated in FIG. 7. In particular, at 701, data representing concentrations of atomic elements (or data pertaining to such elemental concentrations) E is collected for a number of rock samples with mineral component concentrations M. In embodiments, the data sets E and M of block 701 can be determined using well-known laboratory techniques. An example is the determination of mineral concentrations using X-ray diffraction (XRD) or infrared spectroscopy (IR) measurements. Another example is the determination of elemental concentrations using X-ray fluorescence spectroscopy (XRF), mass spectrometry, neutron activation, and the like. In other embodiments, these data can be synthetically constructed for a limited number of minerals and their associated elements. The addition of synthetic data can be used, for example, to expand the range of data and to increase robustness of the derived mapping functions. Optionally, as described below, the uncertainties on the input data may be used in the model to benefit the estimation on uncertainties on the output data.

At 703, the data sets E and M of block 701 (or portions thereof) are used as input to the process of training and optimizing an autoencoder (block 705). The training and optimization of the autoencoder in block 705 can employ unsupervised learning as described herein. The training and optimization process of block 705 can be carried out until the output data E' of the autoencoder satisfactorily matches the input data E as determined in block 707, thereby confirming that the autoencoder has been properly trained. When the training process is complete, the trained autoencoder 709 is deployed for use (e.g., in FIG. 8) in 711.

Figure 8:
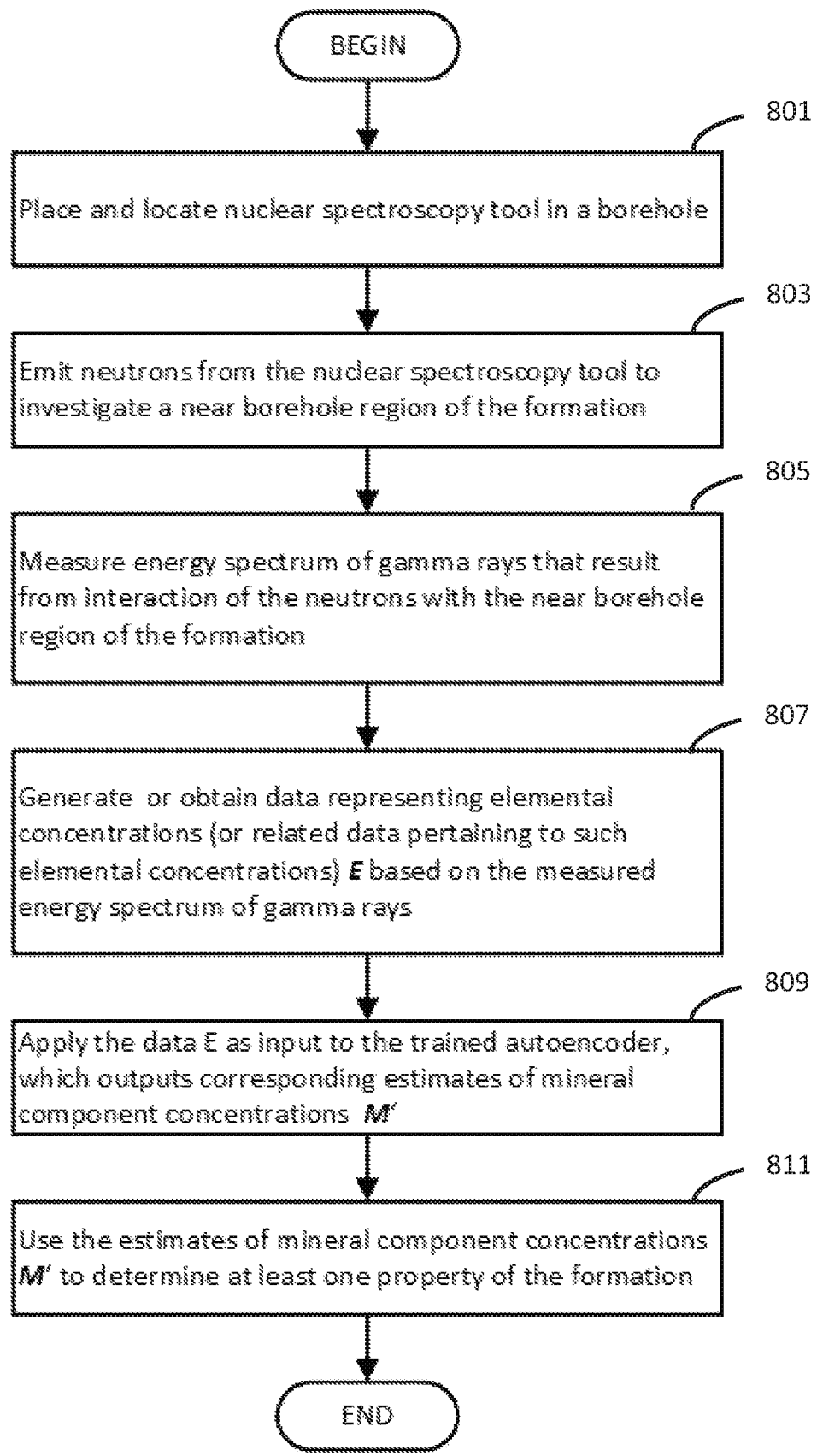
FIG. 8 is a flowchart illustrating an exemplary workflow for estimating mineral component concentrations and possibly other formation properties from data obtained from a spectroscopy logging tool using a trained autoencoder.

Once the autoencoder has been trained, it can be used in conjunction with data obtained by a downhole spectroscopic logging tool to determine an estimate of mineral component concentrations and possibly other formation properties for the near-borehole formation that is investigated by the spectroscopic logging tool as illustrated in the example workflow of FIG. 8.

Thus, as seen in FIG. 8, at 801, a downhole nuclear spectroscopy tool (e.g., as described above with respect to FIGS. 1-3) is placed and located in a borehole.

At 803, the tool is configured and operated to emit neutrons to investigate a near borehole region of the formation.

At 805, the tool is configured and operated to measure the energy spectrum of gamma rays that result from interaction of the neutrons with the near borehole region of the formation.

At 807, the tool is configured and operated to generate or obtain data representing concentrations of atomic elements (or related data pertaining to such elemental concentrations) E based on the measured energy spectrum of gamma rays (block 805).

At 809, the data E of block 807 is used as input to the trained autoencoder, which outputs corresponding estimates of mineral component concentrations M'.

At 811, the estimates of mineral component concentrations M' of block 809 can be used to determine at least one property or parameter that characterizes the formation, such as the formation matrix density ($\rho_{ma}$), formation porosity ($\phi$), formation matrix Sigma, and formation water saturation ($S_w$) as described above, or some other formation property.

In embodiments, the workflow of FIG. 8 can be repeated for nuclear spectroscopy measurements at different depths and/or different azimuth directions in a borehole in order to investigate different parts of the formation that is traversed by the borehole.

In other embodiments, similar nuclear spectroscopy measurements can be performed in a surface laboratory or surface well site on one or more formation rock samples (such as rock chips, rock cores, rock drill cuttings, rock outcrops, or other rock samples) and follow-on data processing operations can use the trained autoencoder to determine estimates of mineral component concentrations M' and one or more formation properties based thereon, such as formation matrix density ($\rho_{ma}$), formation porosity ($\phi$), formation matrix Sigma, and formation water saturation ($S_w$) as described above.

In yet other embodiments, other measurements such as X-ray fluorescence spectroscopy, atomic absorption spectroscopy, mass spectrometry, neutron activation, other measurement(s), or combinations thereof can be used to determine or obtain elemental concentration data (or data corresponding thereto) as well as mineralogy concentration data for formation rock samples that are used to train the autoencoder as well as the follow-on data processing operations can use the trained autoencoder to determine estimates of mineral component concentrations and one or more formation properties based thereon, such as formation matrix density ($\rho_{ma}$), formation porosity ($\phi$), formation matrix Sigma, and formation water saturation ($S_w$) as described above.

In still other embodiments, other ANN architectures can be used in place of or in combination with the autoencoder and trained to determine estimates of mineral component concentrations and one or more formation properties based thereon, such as formation matrix density ($\rho_{ma}$), formation porosity ($\phi$), formation matrix Sigma, and formation water saturation ($S_w$) as described above.

Predicted concentrations of selected mineral components in a set of rock formation samples using an ANN mapping function have been found to correspond well to predictions for the same minerals in the same set of rock formations using an RBF model (Freedman et al., 2014). Furthermore, the ANN mapping function can provide improved statistical performance relative to RBF predictions from elements to minerals and especially fewer outlier results. Specifically, FIGS. 9A-9H are plots of predicted concentrations of selected minerals (quartz, dolomite, orthoclase, plagioclase) in a set of rock formation samples using the RBF model and the autoencoder of FIG. 5. FIG. 9A is a plot of predicted concentrations of quartz in the set of rock formation samples using the RBF model. FIG. 9B is a plot of predicted concentrations of quartz in the set of rock formation samples using the autoencoder of FIG. 5. FIG. 9C is a plot of predicted concentrations of dolomite in the set of rock formation samples using the RBF model. FIG. 9D is a plot of predicted concentrations of dolomite in the set of rock formation samples using the autoencoder of FIG. 5. FIG. 9E is a plot of predicted concentrations of orthoclase in the set of rock formation samples using the RBF model. FIG. 9F is a plot of predicted concentrations of orthoclase in the set of rock formation samples using the autoencoder of FIG. 5. FIG. 9G is a plot of predicted concentrations of plagioclase in the set of rock formation samples using the RBF model. FIG. 9H is a plot of predicted concentrations of plagioclase in the set of rock formation samples using the autoencoder of FIG. 5. These rock formation samples were not part of the input data used to train either the RBF or the autoencoder models and are independent samples with reference (known) mineral concentrations on which to test the accuracy and robustness of the autoencoder model relative to that of published methods. The autoencoder predictions compare favorably to their reference mineral concentrations with low mean absolute error and mean square errors and no obvious systematic error (e.g., bias) in the predictions. The predicted concentrations of quartz and dolomite from both RBF and autoencoder (FIGS. 9A-9D) fall within a few weight percent of their reference values for >95% of the sample population, which is to be expected because quartz and dolomite have simple, stoichiometric mineral formulae and the mapping of elements to quartz and dolomite is well known or predictable. Nonetheless, the autoencoder predictions show improved statistical performance relative to RBF predictions and especially fewer outlier results. The autoencoder predictions for other minerals with more complex and/or variable mineral formulae, such as orthoclase (potassium feldspar) and plagioclase (FIGS. 9E-9H), are demonstrated by the statistical metrics to be much improved over those predictions from RBF, and this can be observed in the graphical plots, for example, by the lesser scatter and bias in the predictions for samples with high concentrations of orthoclase and plagioclase (i.e., arkose formations) and by the fewer number of samples with false-positive or false-negative predictions. Note that the outputs of the autoencoder (or other ANN model) as described herein are not limited to the minerals presently described, and the present disclosure should not be interpreted as limited only to the determination of the aforementioned examples.

Figure 10:
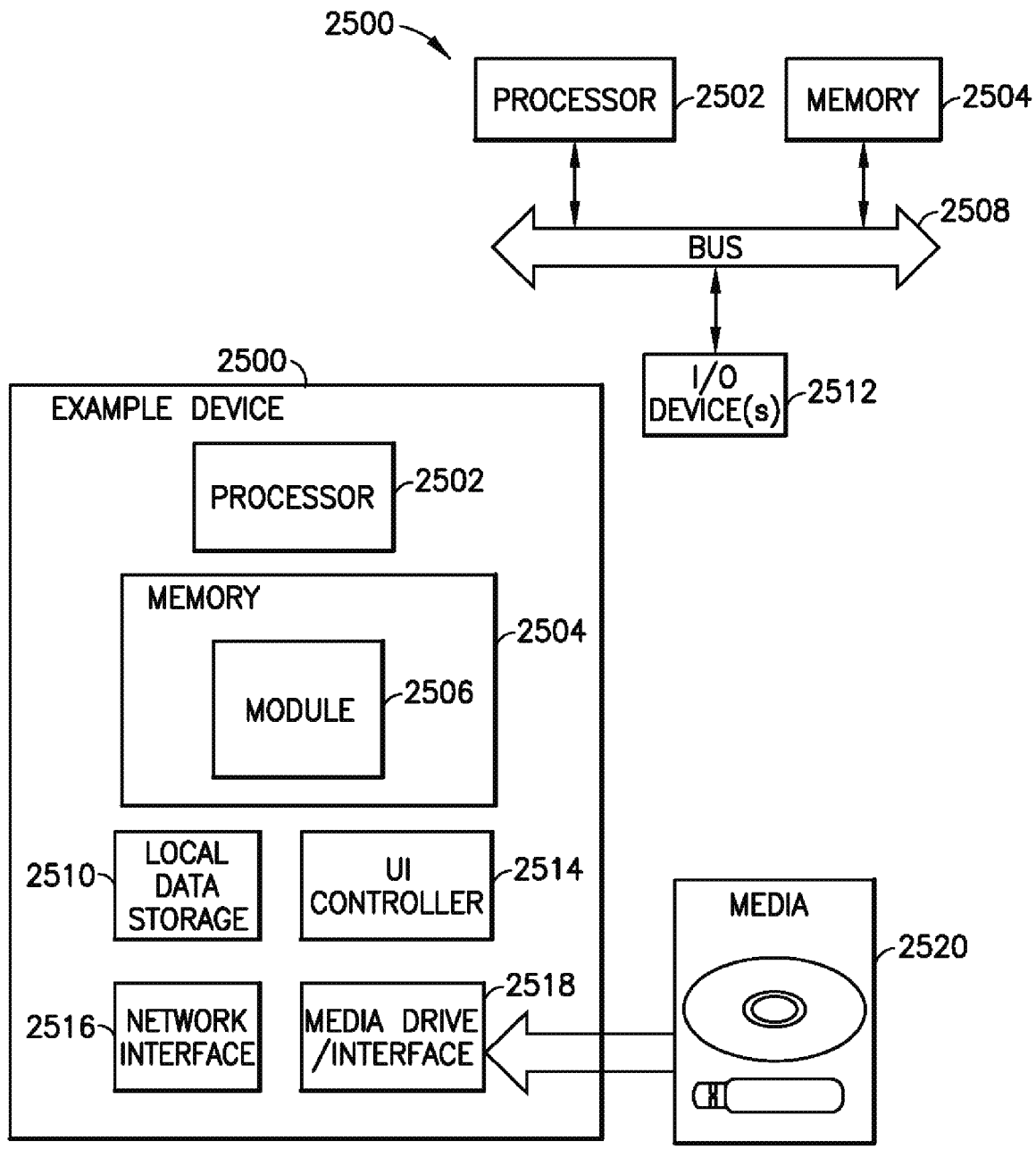
FIG. 10 is a functional block diagram of an exemplary computer processing system.

FIG. 10 illustrates an example device 2500, with a processor 2502 and memory 2504 that can be configured to implement various embodiments of the methodology and systems as discussed in this disclosure. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more of computers, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network.

A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user (such as a human annotator) to enter commands and information to device 2500, and also allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various processes of present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer. Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general-purpose computer) for executing any of the methods and processes described above.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

There have been described and illustrated herein several embodiments of methods and systems that determine an estimate of the mineral concentrations in a geological rock formation from the measurement of the elemental concentrations in the same using an ANN mapping from elements to minerals. While particular embodiments of the invention have been described, it is not intended that the invention be limited thereto, as it is intended that the invention be as broad in scope as the art will allow and that the specification be read likewise. Thus, while particular ANN mappings from elements to minerals based on the encoder part of the trained autoencoder have been disclosed, it will be appreciated that other ANN mappings can be used as well. It will therefore be appreciated by those skilled in the art that yet other modifications could be made to the provided invention without deviating from its spirit and scope as claimed.

What is claimed is:

1. A method for characterizing a geological formation comprising:
  a) generating or obtaining data pertaining to concentrations of a set of atomic elements in a part or sample of the geological formation based on at least one measurement of the part or sample of the geological formation;
  b) using the data of a) as input to a mapping function that derives at least one of i) concentrations of a set of mineral components in the part or sample of the geological formation or ii) reconstructed concentrations of the set of atomic elements in the part or sample of the geological formation, wherein the mapping function is based on training a neural network; and
  c) determining at least one parameter characterizing the part or sample of the geological formation based on the concentrations of the set of mineral components in the part or sample of the geological formation or the reconstructed concentrations of the set of atomic elements in the part or sample of the geological formation,
  wherein the mapping function of b) is derived from minimization of a cost function given a set of data comprising: input data, latent space data, output data, uncertainties in the input data, uncertainties in the latent space data, missing data, and data of different fidelities as captured by their uncertainties.

2. A method according to claim 1, wherein:
the data of a) represents the concentrations of the set of atomic elements in the part or sample of the geological formation or otherwise corresponds to the concentrations of the set of atomic elements in the part or sample of the geological formation.

3. A method according to claim 1, wherein:
the mapping function derives a vector of data representing at least one of mineral component concentrations in the part or sample of the geological formation and reconstructed elemental concentrations in the part or sample of the geological formation.

4. A method according to claim 1, wherein:
the mapping function derives a matrix of data representing at least one of mineral component concentrations in a plurality of parts or samples of the geological formation and reconstructed elemental concentrations in the plurality of parts or samples of the geological formation.

5. A method according to claim 1, wherein:
the part or sample of the geological formation comprises a portion of the geological formation surrounding a borehole, rock core, rock chips, rock drill cuttings, or rock outcrop.

6. A method according to claim 1, wherein:
the at least one measurement of a) measures photon counts attributable to the part or sample of the geological formation.

7. A method according to claim 6, wherein:
the photon counts are selected from the group consisting of X-rays and gamma rays.

8. A method according to claim 1, wherein:
the at least one measurement of a) comprises a nuclear logging measurement.

9. A method according to claim 8, further comprising:
performing the nuclear logging measurement using a nuclear logging device within a borehole that traverses the geological formation.

10. A method according to claim 1, wherein:
the at least one measurement of a) is selected from the group consisting of X-ray fluorescence spectroscopy, atomic absorption spectroscopy, mass spectrometry, neutron activation, other measurement(s), or combinations thereof.

11. A method according to claim 1, wherein:
the at least one parameter characterizing the part or sample of the geological formation is selected from the group consisting of formation matrix density, formation porosity, matrix Sigma, formation saturation, other formation parameter(s), or combinations thereof.

12. A method according to claim 1, wherein:
the cost function is selected from the group consisting of a mean square error function, a least squares error function, a maximum likelihood error function, a mean absolute error function, and a cross-entropy function.

13. A method according to claim 1, wherein:
the cost function optimizes or otherwise accounts for both model (aleatoric) uncertainty and data (epistemic) uncertainty.

14. A method according to claim 1, wherein:
the cost function includes a regularization function to optimize accuracy and robustness.

15. A method according to claim 1, wherein:
the mapping function of b) includes at least one function that determines at least one of i) uncertainties for the concentrations of the set of mineral components in the part or sample of the geological formation, or ii) uncertainties for the reconstructed concentrations of the set of atomic elements in the part or sample of the geological formation.

16. A system for characterizing a geological formation comprising:
a processor configured to
a) generate or obtain from memory data pertaining to concentrations of a set of atomic elements in a part or sample of the geological formation based on at least one measurement of the part or sample of the geological formation;
b) use of the data of a) as input to a mapping function that derives at least one of i) concentrations of a set of mineral components in the part or sample of the geological formation or ii) reconstructed concentrations of the set of atomic elements in the part or sample of the geological formation, wherein the mapping function is based on training a neural network, and
c) determine at least one parameter characterizing the part or sample of the geological formation based on the concentrations of the set of mineral components in the part or sample of the geological formation or the reconstructed concentrations of the set of atomic elements in the part or sample of the geological formation,
wherein the mapping function of b) is derived from minimization of a cost function given a set of data comprising: input data, latent space data, output data, uncertainties in the input data, uncertainties in the latent space data, missing data, and data of different fidelities as captured by their uncertainties.

17. A system according to claim 16, wherein:
the data of a) represents the concentrations of the set of atomic elements in the part or sample of the geological formation or otherwise corresponds to the concentrations of the set of atomic elements in the part or sample of the geological formation.

18. A system according to claim 16, wherein:
the at least one measurement of a) measures photon counts attributable to the part or sample of the geological formation.

19. A system according to claim 18, wherein:
the photon counts are selected from the group consisting of X-rays and gamma rays.

20. The system according to claim 16, wherein:
the cost function is selected from the group consisting of a mean square error function, a least squares error function, a maximum likelihood error function, a mean absolute error function, and a cross-entropy function.

* * * * *